US008198409B2

(12) United States Patent
Sato

(10) Patent No.: US 8,198,409 B2
(45) Date of Patent: Jun. 12, 2012

(54) POLYPEPTIDE, AN AFFINITY CHROMATOGRAPHY MATERIAL, AND A METHOD FOR SEPARATING AND/OR PURIFYING IMMUNOGLOBULIN

(75) Inventor: Satoshi Sato, Okayama (JP)

(73) Assignee: Nomadic Bioscience Co., Ltd., Okayama City (JP)

( * ) Notice: Subject to any disclaimer, the term of this patent is extended or adjusted under 35 U.S.C. 154(b) by 377 days.

(21) Appl. No.: 12/600,828

(22) PCT Filed: May 18, 2008

(86) PCT No.: PCT/JP2008/059091

§ 371 (c)(1),
(2), (4) Date: Nov. 18, 2009

(87) PCT Pub. No.: WO2008/143199

PCT Pub. Date: Nov. 27, 2008

(65) Prior Publication Data

US 2010/0168395 A1 Jul. 1, 2010

(30) Foreign Application Priority Data

May 21, 2007 (JP) ................................ 2007-133778

(51) Int. Cl.
*C07K 14/00* (2006.01)

(52) U.S. Cl. ....................................... 530/385; 530/350

(58) Field of Classification Search .................. 530/385, 530/350

See application file for complete search history.

(56) References Cited

U.S. PATENT DOCUMENTS

| | | | |
|---|---|---|---|
| 5,580,788 | A | 12/1996 | Kihira et al. |
| 2005/0143566 | A1 | 6/2005 | Hober |
| 2006/0194950 | A1 | 8/2006 | Hober et al. |
| 2006/0194955 | A1 | 8/2006 | Hober et al. |

FOREIGN PATENT DOCUMENTS

| | | | |
|---|---|---|---|
| JP | 5-51399 | A | 3/1993 |
| JP | 2005-538693 | A | 12/2005 |

OTHER PUBLICATIONS

Nicola L. Brown et al.; "A Study of the Interactions Between an IgG-Binding Domain Based on the B Domain of Staphylococcal Protein A and Rabbit IgG"; Molecular Biotechnology, vol. 10, 1998, pp. 9-16.

Satoshi Sato et al.; "Phi-Analysis of the Folding of the B Domain of Protein A Using Multiple Optical Probes"; Journal of Molecular Biology, vol. 360, 2006, pp. 850-864.

Pooja Arora et al.; "Fast and faster: A design variant of the B-domain of protein a folds in 3 microsec"; Protein Science, vol. 13, 2004, pp. 847-853.

Satoshi Sato; "Analysis of the protein folding transition state by introducing amino acid mutations"; Protein, nucleic acid and enzyme, vol. 49, No. 14, 2004, pp. 2230-2234.

Satoshi Sato et al.; "Searching for Multiple Folding Pathways of a Nearly Symmetrical Protein: Temperature Dependent Phi-value Analysis of the B Domain of Protein A"; Journal of Molecular Biology, vol. 372, 2007, pp. 254-267.

Satoshi Sato et al.; "Testing protein-folding simulations by experiment: B domain of protein A"; PNAS, vol. 101, No. 18, May 4, 2004, pp. 6952-6956.

Susanne Gulich et al.; "Protein engineering of an IgG-binding domain allows milder elution conditions during affinity chromatography"; Journal of Biotechnology, vol. 76, 2000, pp. 233-244.

International Search Report of PCT/JP2008/059091, date of mailing Aug. 5, 2008.

*Primary Examiner* — Karen Carlson

(74) *Attorney, Agent, or Firm* — Westerman, Hattori, Daniels & Adrian, LLP

(57) ABSTRACT

A mutant of the polypeptide Protein A, wherein immunoglobulin binding properties can be altered by changing temperature under the conditions of pH 5-9, below 60° C. The use of the mutant Protein A include the use thereof as a ligand coupled to an affinity chromatography support for the purification of immunoglobulins by affinity chromatography, wherein the immunoglobulins is eluted by changing temperature and thereby the conformation of the mutant Protein A.

2 Claims, 5 Drawing Sheets

[Figure 1]
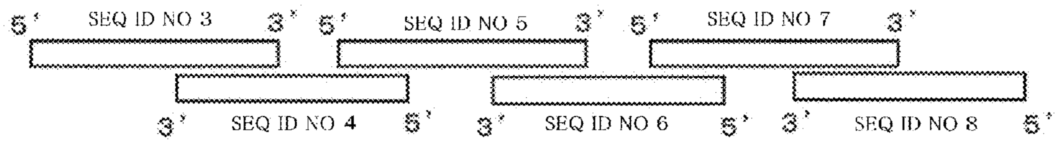
[Figure 2]
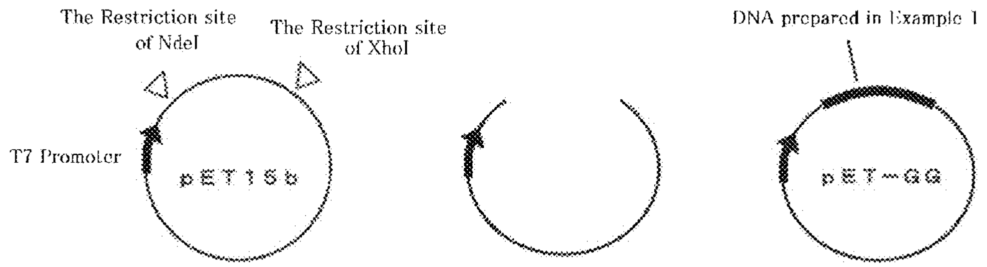
[Figure 3]
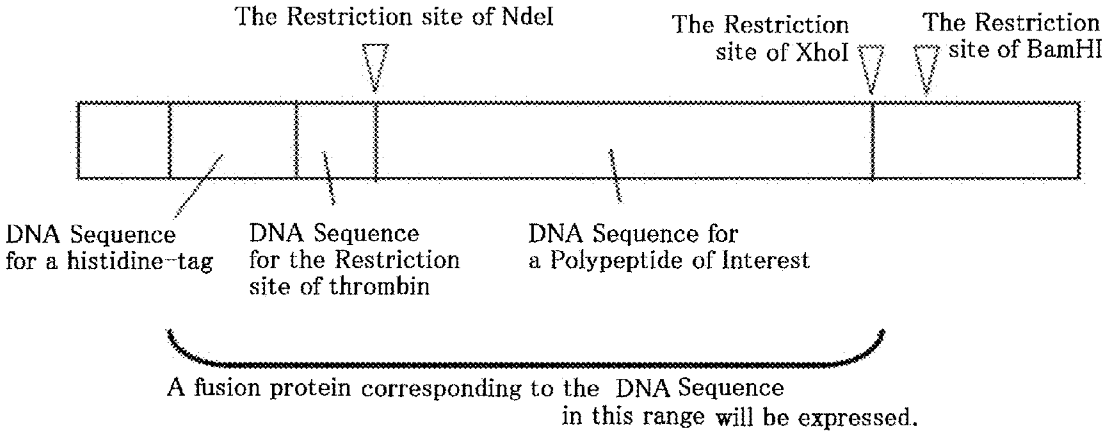

[Figure 4]
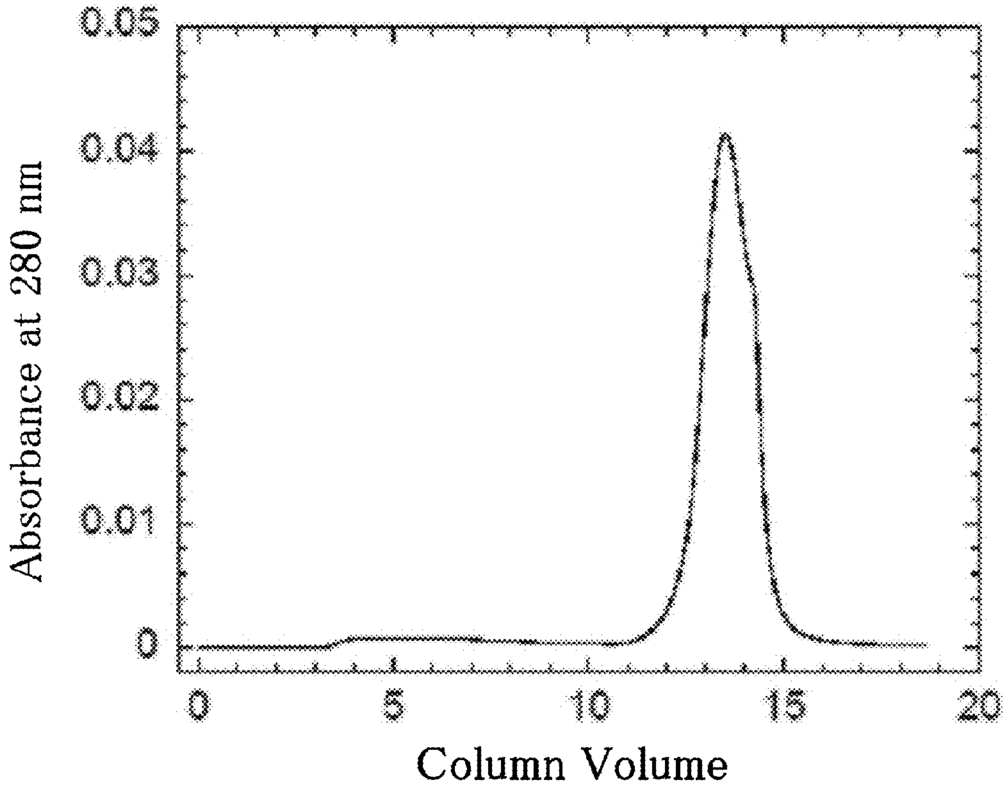

[Figure 5]
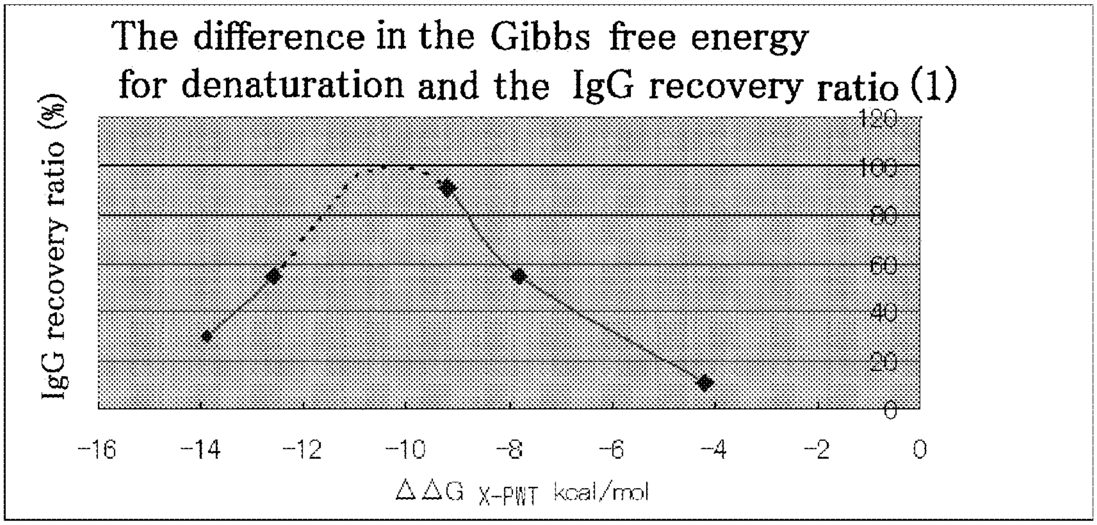

[Figure 6]
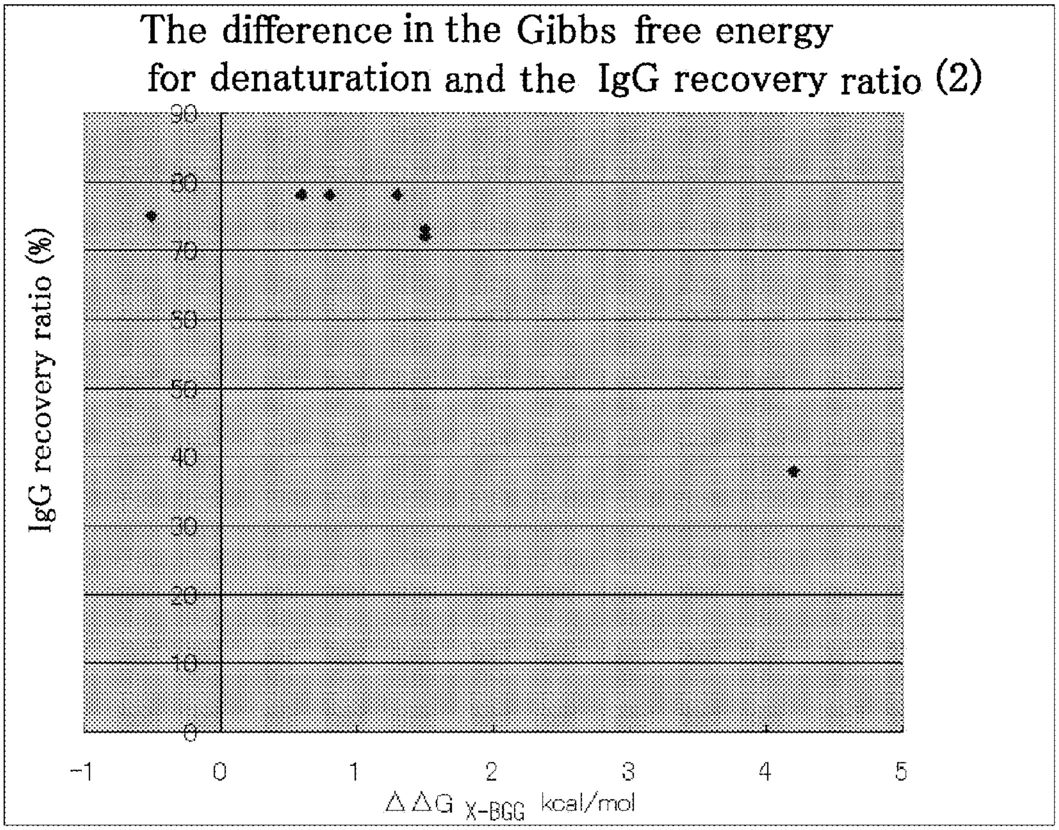

[Figure 7]

SEQ ID NO 1

Ala Asp Asn Lys Phe Asn Lys Glu Gln Gln Asn Ala Phe Tyr Glu Ile
1 5 10 15

Leu His Leu Pro Asn Leu Asn Glu Glu Gln Arg Asn Gly Phe Ile Gln
20 25 30

Ser Leu Lys Asp Asp Pro Ser Gln Ser Ala Asn Leu Leu Ala Glu Ala
35 40 45

Lys Lys Leu Asn Asp Ala Gln Ala Pro Lys Ala
50 55

SEQ ID NO 2

Ala Asp Asn Lys Phe Asn Lys Glu Gln Gln Asn Ala Phe Tyr Glu Ile
1 5 10 15

Leu His Leu Pro Asn Leu Asn Glu Glu Gln Arg Asn Ala Phe Ile Gln
20 25 30

Ser Leu Lys Asp Asp Pro Ser Gln Ser Ala Asn Leu Leu Ala Glu Ala
35 40 45

Lys Lys Leu Asn Asp Ala Gln Ala Pro Lys Ala
50 55

SEQ ID NO 9

Ala Asp Asn Lys Phe Asn Lys Glu Gln Gln Asn Ala Phe Tyr Glu Ile
1 5 10 15

Leu His Gly Pro Asn Gly Asn Glu Glu Gln Arg Asn Ala Phe Ile Gln
20 25 30

Ser Leu Lys Asp Asp Pro Ser Gln Ser Ala Asn Leu Leu Ala Glu Ala
35 40 45

Lys Lys Leu Asn Asp Ala Gln Ala Pro Lys Ala
50 55

SEQUENCE LISTING

<160> NUMBER OF SEQ ID NOS: 46

<210> SEQ ID NO 1
<211> LENGTH: 59
<212> TYPE: PRT
<213> ORGANISM: Staphylococcus
<220> FEATURE:
<221> NAME/KEY: DOMAIN
<222> LOCATION: (1)..(59)
<223> OTHER INFORMATION: B domain of Protein A

<400> SEQUENCE: 1

```
Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala
    50                  55
```

<210> SEQ ID NO 2
<211> LENGTH: 59
<212> TYPE: PRT
<213> ORGANISM: Artificial
<220> FEATURE:
<223> OTHER INFORMATION: Mutant of B domain of Protein A: PWT

<400> SEQUENCE: 2

```
Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala
    50                  55
```

<210> SEQ ID NO 3
<211> LENGTH: 43
<212> TYPE: DNA
<213> ORGANISM: Artificial
<220> FEATURE:
<223> OTHER INFORMATION: fragment of B domain mutant (BGG) gene
<220> FEATURE:
<223> OTHER INFORMATION: Inventor: Sato, Satoshi

<400> SEQUENCE: 3

```
gtgccgcgcc atatggccga taacaaattt aataaagaac agc                      43
```

<210> SEQ ID NO 4
<211> LENGTH: 57
<212> TYPE: DNA
<213> ORGANISM: Artificial
<220> FEATURE:
<223> OTHER INFORMATION: fragment of B domain mutant (BGG) gene

<400> SEQUENCE: 4

```
cggaccatgc aagatctcat agaacgcatt ttgctgttct ttattaaatt tgttatc        57
```

<210> SEQ ID NO 5
<211> LENGTH: 61
<212> TYPE: DNA

<213> ORGANISM: Artificial
<220> FEATURE:
<223> OTHER INFORMATION: fragment of B domain mutant (BGG) gene

<400> SEQUENCE: 5
ctatgagatc ttgcatggtc cgaatggcaa tgaggaacaa cgtaacgcgt ttattcagtc 60
t 61

<210> SEQ ID NO 6
<211> LENGTH: 60
<212> TYPE: DNA
<213> ORGANISM: Artificial
<220> FEATURE:
<223> OTHER INFORMATION: fragment of B domain mutant (BGG) gene

<400> SEQUENCE: 6
caggttggcg ctctgactcg gatcatcctt gagagactga ataaacgcgt tacgttgttc 60

<210> SEQ ID NO 7
<211> LENGTH: 57
<212> TYPE: DNA
<213> ORGANISM: Artificial
<220> FEATURE:
<223> OTHER INFORMATION: fragment of B domain mutant (BGG) gene

<400> SEQUENCE: 7
ccgagtcaga gcgccaacct gttagctgaa gcgaagaaac tgaacgatgc acaggcg 57

<210> SEQ ID NO 8
<211> LENGTH: 57
<212> TYPE: DNA
<213> ORGANISM: Artificial
<220> FEATURE:
<223> OTHER INFORMATION: fragment of B domain mutant (BGG) gene

<400> SEQUENCE: 8
gtacagccgg gactcgagtt acgctttagg cgcctgtgca tcgttcagtt tcttcgc 57

<210> SEQ ID NO 9
<211> LENGTH: 59
<212> TYPE: PRT
<213> ORGANISM: Artificial
<220> FEATURE:
<223> OTHER INFORMATION: B domain mutant (BGG)

<400> SEQUENCE: 9

```
Ala Asp Asn Lys Phe Asn Lys Glu Gln Gln Asn Ala Phe Tyr Glu Ile
1               5                   10                  15

Leu His Gly Pro Asn Gly Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala
    50                  55
```

<210> SEQ ID NO 10
<211> LENGTH: 59
<212> TYPE: PRT
<213> ORGANISM: Artificial
<220> FEATURE:
<223> OTHER INFORMATION: B domain mutant (BGG11)

<400> SEQUENCE: 10

```
Ala Asp Asn Lys Phe Asn Lys Glu Gln Gln Asn Ala Phe Tyr Glu Ile
1               5                   10                  15
```

-continued

Leu His Ala Pro Asn Gly Asn Glu Glu Gln Arg Asn Ala Phe Ile Gln
20 25 30

Ser Leu Lys Asp Asp Pro Ser Gln Ser Ala Asn Leu Leu Ala Glu Ala
35 40 45

Lys Lys Leu Asn Asp Ala Gln Ala Pro Lys Ala
50 55

<210> SEQ ID NO 11
<211> LENGTH: 59
<212> TYPE: PRT
<213> ORGANISM: Artificial
<220> FEATURE:
<223> OTHER INFORMATION: B domain mutant (BGG12)

<400> SEQUENCE: 11

Ala Asp Asn Lys Phe Asn Lys Glu Gln Gln Asn Ala Phe Tyr Glu Ile
1 5 10 15

Leu His Leu Pro Asn Gly Asn Glu Glu Gln Arg Asn Ala Phe Ile Gln
20 25 30

Ser Leu Lys Asp Asp Pro Ser Gln Ser Ala Asn Leu Leu Ala Glu Ala
35 40 45

Lys Lys Leu Asn Asp Ala Gln Ala Pro Lys Ala
50 55

<210> SEQ ID NO 12
<211> LENGTH: 59
<212> TYPE: PRT
<213> ORGANISM: Artificial
<220> FEATURE:
<223> OTHER INFORMATION: B domain mutant (BGG13)

<400> SEQUENCE: 12

Ala Asp Asn Lys Phe Asn Lys Glu Gln Gln Asn Ala Phe Tyr Glu Ile
1 5 10 15

Leu His Gly Pro Asn Ala Asn Glu Glu Gln Arg Asn Ala Phe Ile Gln
20 25 30

Ser Leu Lys Asp Asp Pro Ser Gln Ser Ala Asn Leu Leu Ala Glu Ala
35 40 45

Lys Lys Leu Asn Asp Ala Gln Ala Pro Lys Ala
50 55

<210> SEQ ID NO 13
<211> LENGTH: 59
<212> TYPE: PRT
<213> ORGANISM: Artificial
<220> FEATURE:
<223> OTHER INFORMATION: B domain mutant (BGG14)

<400> SEQUENCE: 13

Ala Asp Asn Lys Phe Asn Lys Glu Gln Gln Asn Ala Phe Tyr Glu Ile
1 5 10 15

Leu His Gly Pro Asn Leu Asn Glu Glu Gln Arg Asn Ala Phe Ile Gln
20 25 30

Ser Leu Lys Asp Asp Pro Ser Gln Ser Ala Asn Leu Leu Ala Glu Ala
35 40 45

Lys Lys Leu Asn Asp Ala Gln Ala Pro Lys Ala
50 55

<210> SEQ ID NO 14
<211> LENGTH: 59
<212> TYPE: PRT

-continued

```
<213> ORGANISM: Artificial
<220> FEATURE:
<223> OTHER INFORMATION: B domain mutant (BGG17)

<400> SEQUENCE: 14

Ala Asp Asn Lys Phe Asn Lys Glu Gln Gln Asn Ala Phe Tyr Glu Ile
1               5                   10                  15

Leu His Ala Pro Asn Ala Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala
    50                  55


<210> SEQ ID NO 15
<211> LENGTH: 59
<212> TYPE: PRT
<213> ORGANISM: Artificial
<220> FEATURE:
<223> OTHER INFORMATION: B domain mutant (BLG18)

<400> SEQUENCE: 15

Ala Asp Asn Lys Phe Asn Lys Glu Gln Gln Asn Ala Phe Tyr Glu Ile
1               5                   10                  15

Leu His Leu Pro Asn Gly Asn Glu Glu Gln Arg Asn Ala Ala Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala
    50                  55


<210> SEQ ID NO 16
<211> LENGTH: 59
<212> TYPE: PRT
<213> ORGANISM: Artificial
<220> FEATURE:
<223> OTHER INFORMATION: B domain mutant (BLG19)

<400> SEQUENCE: 16

Ala Asp Asn Lys Phe Asn Lys Glu Gln Gln Asn Ala Phe Tyr Glu Ile
1               5                   10                  15

Leu His Leu Pro Asn Gly Asn Glu Glu Gln Arg Asn Ala Gly Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala
    50                  55


<210> SEQ ID NO 17
<211> LENGTH: 59
<212> TYPE: PRT
<213> ORGANISM: Artificial
<220> FEATURE:
<223> OTHER INFORMATION: B domain mutant (BLG21)

<400> SEQUENCE: 17

Ala Asp Asn Lys Phe Asn Lys Glu Gln Gln Asn Ala Phe Tyr Glu Ile
1               5                   10                  15

Leu His Leu Pro Asn Gly Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45
```

```
Lys Lys Gly Asn Asp Ala Gln Ala Pro Lys Ala
    50                  55


<210> SEQ ID NO 18
<211> LENGTH: 59
<212> TYPE: PRT
<213> ORGANISM: Artificial
<220> FEATURE:
<223> OTHER INFORMATION: B domain mutant (BLG28)

<400> SEQUENCE: 18

Ala Asp Asn Lys Phe Asn Lys Glu Gln Gln Asn Ala Phe Tyr Glu Ile
1               5                   10                  15

Leu His Leu Pro Asn Gly Asn Glu Glu Gly Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala
    50                  55


<210> SEQ ID NO 19
<211> LENGTH: 59
<212> TYPE: PRT
<213> ORGANISM: Artificial
<220> FEATURE:
<223> OTHER INFORMATION: B domain mutant (BLG32)

<400> SEQUENCE: 19

Ala Asp Asn Lys Phe Asn Lys Glu Gln Gln Asn Ala Phe Tyr Glu Ile
1               5                   10                  15

Leu His Leu Pro Asn Gly Asn Glu Glu Gln Gly Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala
    50                  55


<210> SEQ ID NO 20
<211> LENGTH: 59
<212> TYPE: PRT
<213> ORGANISM: Artificial
<220> FEATURE:
<223> OTHER INFORMATION: B domain mutant (BGA19)

<400> SEQUENCE: 20

Ala Asp Asn Lys Phe Asn Lys Glu Gln Gln Asn Ala Phe Tyr Glu Ile
1               5                   10                  15

Leu His Gly Pro Asn Ala Asn Glu Glu Gln Arg Asn Ala Gly Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala
    50                  55


<210> SEQ ID NO 21
<211> LENGTH: 59
<212> TYPE: PRT
<213> ORGANISM: Artificial
<220> FEATURE:
<223> OTHER INFORMATION: B domain mutant (BGA21)

<400> SEQUENCE: 21
```

-continued

```
Ala Asp Asn Lys Phe Asn Lys Glu Gln Gln Asn Ala Phe Tyr Glu Ile
1               5                   10                  15

Leu His Gly Pro Asn Ala Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Gly Asn Asp Ala Gln Ala Pro Lys Ala
    50                  55


<210> SEQ ID NO 22
<211> LENGTH: 42
<212> TYPE: DNA
<213> ORGANISM: Artificial
<220> FEATURE:
<223> OTHER INFORMATION: Primer for PWT

<400> SEQUENCE: 22

tatgagatct tgcatcttcc gaatctgaat gaggaacaac gt                       42


<210> SEQ ID NO 23
<211> LENGTH: 42
<212> TYPE: DNA
<213> ORGANISM: Artificial
<220> FEATURE:
<223> OTHER INFORMATION: Primer for PWT

<400> SEQUENCE: 23

acgttgttcc tcattcagat tcggaagatg caagatctca ta                       42


<210> SEQ ID NO 24
<211> LENGTH: 33
<212> TYPE: DNA
<213> ORGANISM: Artificial
<220> FEATURE:
<223> OTHER INFORMATION: Primer for BGG11

<400> SEQUENCE: 24

tatgagatct tgcatgctcc gaatggcaat gag                                 33


<210> SEQ ID NO 25
<211> LENGTH: 33
<212> TYPE: DNA
<213> ORGANISM: Artificial
<220> FEATURE:
<223> OTHER INFORMATION: Primer for BGG11

<400> SEQUENCE: 25

ctcattgcca ttcggagcat gcaagatctc ata                                 33


<210> SEQ ID NO 26
<211> LENGTH: 33
<212> TYPE: DNA
<213> ORGANISM: Artificial
<220> FEATURE:
<223> OTHER INFORMATION: Primer for BGG12

<400> SEQUENCE: 26

tatgagatct tgcatcttcc gaatggcaat gag                                 33


<210> SEQ ID NO 27
<211> LENGTH: 33
<212> TYPE: DNA
<213> ORGANISM: Artificial
<220> FEATURE:
<223> OTHER INFORMATION: Primer for BGG12
```

<400> SEQUENCE: 27
ctcattgcca ttcggaagat gcaagatctc ata 33

<210> SEQ ID NO 28
<211> LENGTH: 33
<212> TYPE: DNA
<213> ORGANISM: Artificial
<220> FEATURE:
<223> OTHER INFORMATION: Primer for BGG13

<400> SEQUENCE: 28
ttgcatggtc cgaatgccaa tgaggaacaa cgt 33

<210> SEQ ID NO 29
<211> LENGTH: 33
<212> TYPE: DNA
<213> ORGANISM: Artificial
<220> FEATURE:
<223> OTHER INFORMATION: Primer for BGG13

<400> SEQUENCE: 29
acgttgttcc tcattggcat tcggaccatg caa 33

<210> SEQ ID NO 30
<211> LENGTH: 33
<212> TYPE: DNA
<213> ORGANISM: Artificial
<220> FEATURE:
<223> OTHER INFORMATION: Primer for BGG14

<400> SEQUENCE: 30
ttgcatggtc cgaatctcaa tgaggaacaa cgt 33

<210> SEQ ID NO 31
<211> LENGTH: 33
<212> TYPE: DNA
<213> ORGANISM: Artificial
<220> FEATURE:
<223> OTHER INFORMATION: Primer for BGG14

<400> SEQUENCE: 31
acgttgttcc tcattgagat tcggaccatg caa 33

<210> SEQ ID NO 32
<211> LENGTH: 42
<212> TYPE: DNA
<213> ORGANISM: Artificial
<220> FEATURE:
<223> OTHER INFORMATION: Primer for BGG17

<400> SEQUENCE: 32
tatgagatct tgcatgctcc gaatgcgaat gaggaacaac gt 42

<210> SEQ ID NO 33
<211> LENGTH: 42
<212> TYPE: DNA
<213> ORGANISM: Artificial
<220> FEATURE:
<223> OTHER INFORMATION: Primer for BGG17

<400> SEQUENCE: 33
acgttgttcc tcattcgcat tcggagcatg caagatctca ta 42

<210> SEQ ID NO 34
<211> LENGTH: 33
<212> TYPE: DNA

<213> ORGANISM: Artificial
<220> FEATURE:
<223> OTHER INFORMATION: Primer for BLG18

<400> SEQUENCE: 34
gaacaacgta acgcggctat tcagtctctc aag 33

<210> SEQ ID NO 35
<211> LENGTH: 33
<212> TYPE: DNA
<213> ORGANISM: Artificial
<220> FEATURE:
<223> OTHER INFORMATION: Primer for BLG18

<400> SEQUENCE: 35
cttgagagac tgaatagccg cgttacgttg ttc 33

<210> SEQ ID NO 36
<211> LENGTH: 33
<212> TYPE: DNA
<213> ORGANISM: Artificial
<220> FEATURE:
<223> OTHER INFORMATION: Primer for BLG19

<400> SEQUENCE: 36
gaacaacgta acgcgggtat tcagtctctc aag 33

<210> SEQ ID NO 37
<211> LENGTH: 33
<212> TYPE: DNA
<213> ORGANISM: Artificial
<220> FEATURE:
<223> OTHER INFORMATION: Primer for BLG19

<400> SEQUENCE: 37
cttgagagac tgaatacccg cgttacgttg ttc 33

<210> SEQ ID NO 38
<211> LENGTH: 33
<212> TYPE: DNA
<213> ORGANISM: Artificial
<220> FEATURE:
<223> OTHER INFORMATION: Primer for BLG21

<400> SEQUENCE: 38
gctgaagcga agaaaggtaa cgatgcacag gcg 33

<210> SEQ ID NO 39
<211> LENGTH: 33
<212> TYPE: DNA
<213> ORGANISM: Artificial
<220> FEATURE:
<223> OTHER INFORMATION: Primer for BLG21

<400> SEQUENCE: 39
cgcctgtgca tcgttacctt tcttcgcttc agc 33

<210> SEQ ID NO 40
<211> LENGTH: 33
<212> TYPE: DNA
<213> ORGANISM: Artificial
<220> FEATURE:
<223> OTHER INFORMATION: Primer for BLG28

<400> SEQUENCE: 40
aatggcaatg aggaaggccg taacgcgttt att 33

<210> SEQ ID NO 41
<211> LENGTH: 33
<212> TYPE: DNA
<213> ORGANISM: Artificial
<220> FEATURE:
<223> OTHER INFORMATION: Primer for BLG28

<400> SEQUENCE: 41
aataaacgcg ttacggcctt cctcattgcc att 33

<210> SEQ ID NO 42
<211> LENGTH: 33
<212> TYPE: DNA
<213> ORGANISM: Artificial
<220> FEATURE:
<223> OTHER INFORMATION: Primer for BLG32

<400> SEQUENCE: 42
ggcaatgagg aacaaggcaa cgcgtttatt cag 33

<210> SEQ ID NO 43
<211> LENGTH: 33
<212> TYPE: DNA
<213> ORGANISM: Artificial
<220> FEATURE:
<223> OTHER INFORMATION: Primer for BLG32

<400> SEQUENCE: 43
ctgaataaac gcgttgcctt gttcctcatt gcc 33

<210> SEQ ID NO 44
<211> LENGTH: 33
<212> TYPE: DNA
<213> ORGANISM: Artificial
<220> FEATURE:
<223> OTHER INFORMATION: Primer for NT23BGG13

<400> SEQUENCE: 44
catggtccga atgccactga ggaacaacgt aac 33

<210> SEQ ID NO 45
<211> LENGTH: 33
<212> TYPE: DNA
<213> ORGANISM: Artificial
<220> FEATURE:
<223> OTHER INFORMATION: Primer for NT23BGG13

<400> SEQUENCE: 45
gttacgttgt tcctcagtgg cattcggacc atg 33

<210> SEQ ID NO 46
<211> LENGTH: 59
<212> TYPE: PRT
<213> ORGANISM: Artificial
<220> FEATURE:
<223> OTHER INFORMATION: B domain mutant (NT23BGG13)

<400> SEQUENCE: 46

Ala Asp Asn Lys Phe Asn Lys Glu Gln Gln Asn Ala Phe Tyr Glu Ile
1 5 10 15

Leu His Gly Pro Asn Ala Thr Glu Glu Gln Arg Asn Ala Phe Ile Gln
20 25 30

-continued

```
Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala
    50                  55
```

POLYPEPTIDE, AN AFFINITY CHROMATOGRAPHY MATERIAL, AND A METHOD FOR SEPARATING AND/OR PURIFYING IMMUNOGLOBULIN

FIELD OF THE INVENTION

This invention relates to a polypeptide capable of binding to a region outside of the complementarity determining regions of immunoglobulin, and more specifically relates to Protein A, or its immunoglobulin binding domains to which an amino acid mutation(s) is introduced such that the loss and formation of the conformation of Protein A, which is a ligand for separation and/or purification of immunoglobulin, can be controlled under the conditions where the immunoglobulin to be separated and/or purified retains its stable conformation and unwanted effects on it such as damage and loss of its function does not occur (pH 5-9, below 60° C.). The invention further relates to an affinity chromatography material in which a mutant of the immunoglobulin binding domain of Protein A having the characteristics described above is used, as well as the use thereof.

BACKGROUND OF THE INVENTION

Immunoglobulin is a collective term for an antibody which recognizes invading foreign substances into the body of animal, etc. to trigger an immunoreaction, and a functionally and/or structurally similar polypeptide thereof, including types of IgG, IgM, IgA, IgD, IgE, and so on. In the fields of life science research, pharmaceuticals, and the laboratory testing, etc., there is an increasing demand for highly pure immunoglobulin.

Affinity chromatography is used as a core technology for a method of removing impurities to produce highly pure immunoglobulin.

In affinity chromatography, a polypeptide with high purity and high concentration can be purified through the following steps of (A)-(C):

(A) A step of loading a sample containing impurities into a column (loading step).

(B) A step of removing the impurities other than the polypeptide to be purified, from the loaded column (washing step).

(C) A step of collecting the polypeptide to be purified, from the column (elution step).

In that regard, in the loading and washing steps, it is essential that the environment inside the column is to set so that the polypeptide to be purified can tightly bind to an affinity ligand, whereas the internal environment of the column is changed in the elution step so that the both are dissociated, wherein the change in pH is usually used for this environmental change.

As a ligand for affinity chromatography used in purification of immunoglobulin, Protein A from *Staphylococcus* (hereafter referred to as Protein A) and its immunoglobulin binding domains which possess remarkably high specificity and affinity to the common region of immunoglobulin have been known and widely used in the manufacturing process of immunoglobulin in industrial scale.

However, there are problems resulting from the nature of immunoglobulin in the affinity chromatography where Protein A or a part thereof is used as a ligand, imposing limitations to the manufacture of immunoglobulin.

In order to carry out elution of immunoglobulin from a column by means of a pH change, a neutral pH range of 6-8 (pH used in the loading/washing steps), where the affinity between immunoglobulin and Protein A is high, needs to be changed to an acidic pH range of 3 to 4 (pH used in the elution step) where the affinity becomes very low. One of the problems is that final yield for the separation/purification of "immunoglobulin with native properties retained" may be significantly worsened in such an acidic range of pH since the change in the immunoglobulin conformation, i.e. association/aggregation may occur and compromise the functions (See Japanese Unexamined Patent Publication (Kokai) No. 2005-206602). In particular, humanized or human IgG, which is industrially most useful, e.g. used as monoclonal antibody drugs, has a higher affinity with Protein A than that of other immunoglobulins and thus requires a buffer with very strong acidity when eluted, leading to more probable association/aggregation. Therefore the inactivation of these IgGs has been a common problem in the art.

For example, supports used in industrial scale on which Protein A or its immunoglobulin binding domain is immobilized as an affinity ligand are available from GE healthcare biosciences, Millipore, etc. The manufacture of immunoglobulin using these supports also uses an acidic elution buffer (pH 3-4) upon elution.

Therefore, it is desired to develop a purification method which does not use acid pH in order to efficiently manufacture highly pure immunoglobulin.

Although various conventional techniques have been tried in order to solve the problem, they have the following problems and do not have much practical utility.

Methods by Adding Additives

The methods in which various kinds of additives are added to allow for elution at pH 5 to pH 7 in using Protein A, have problems such as low recovery ratios, unwanted effects due to the additives themselves, the necessity of removal of the additives with a charge (since they become an obstacle when ion exchange chromatography is used for industrial purification), remaining concern for damages on immunoglobulin at the elution pH of around 5, etc, and thus they have not been practical.

Methods Using of an Artificial Ligand Instead of Protein A

The methods using organic-chemically synthesized artificial ligands as alternatives of Protein A have disadvantages such as a) a significantly low enrichment factor due to slow elution, resulting in very inefficient purification, b) the necessity of concomitant use of additives (which is against the purpose of purification), and c) a poor ability to remove impurities.

Methods Using Shortened Time of Contact to an Acidic Solution

Although there are methods in which the contact time of antibody to an acidic solution is shortened, methods in which a high-concentration of neutral buffer is immediately mixed into an eluate, etc., these can not be a fundamental solution against association/aggregation of antibodies.

Methods Using a Mutant of Protein A as a Ligand

A method using a mutant of Protein A in which a hydrophobic amino acid in the immunoglobulin binding domain is replaced with a histidine to allow for elution at pH 5 (non-patent literature 1), leaves a concern for damages on immunoglobulin because it still uses acidic pH even though the pH is closer to neutral than that used for the naturally occurring version. In addition, the elution is too slow for an industrial process.

Methods in which the Three Dimensional Structure of Protein A is Destabilized (1)

On the other hand, losing the three dimensional structure of a polypeptide used as a ligand can be envisioned in order to disengage immunoglobulin from the ligand. The three dimensional structure of a polypeptide can be usually lost by adding a denaturant such as urea and guanidinium chloride, by increasing temperature, by removing a cofactor, or by changing salt concentration. In particular denaturants and temperature are effective for denaturing many polypeptides.

However, any of the above methods will cause the loss of the three dimensional structure of immunoglobulin to be purified, as well as that of Protein A or its domain, resulting in the irreversible loss of the biological functions of immunoglobulin.

Therefore, it is difficult to find a condition where the three dimensional structure of a ligand polypeptide alone is lost while immunoglobulin to be purified retains its three dimensional structure and its functions if the ligand polypeptide remains the wild type.

Methods in which the Three Dimensional Structure of Protein A is Destabilized (2)

In Z domain where a part of the amino acid sequence of B domain, one of the immunoglobulin binding domains of Protein A, is mutated, a mutant in which 6 glycines are inserted into the Loop 2 portion or a mutant in which the Loop 2 sequence is replaced by glycines became more unstable than Z domain in terms of the three dimensional structure. When this mutant is used, it is possible to elute immunoglobulin at pH 4.5 (non-patent literature 2). However, a concern for damages on immunoglobulin remains because it still uses acidic pH even though the pH is closer to neutral than the used for the naturally occurring version.

Methods in which the Three Dimensional Structure of Protein A is Destabilized (3)

It is known that Protein A is comprised of domains called E, D, A, B, and C domain each of which has about 60 amino acids, and these domains showing high homology each other can bind to the common region (Fc region) of immunoglobulin independently.

The mutant Z domain described above is derived from B domain (SEQ ID NO 1) by replacing Ala at position 1 with Val and Gly at position 29 with Ala in order to remove recognition sequences of polypeptide restriction enzymes. It is known that Z domain also binds to the common region (Fc region) of immunoglobulin either in a single domain configuration or in a multiple domain configuration.

However, the three dimensional structure of these B and Z domains is extremely stable, and even at pH 4 or lower and/or at a high temperature of 60° C. or above where immunoglobulin become unstable, their three dimensional structure is stable. Therefore, it is difficult to selectively destabilize only the three dimensional structure of these domains, which are ligands, by changing temperature without altering the three dimensional structure of immunoglobulin.

Each of immunoglobulin binding domains of said Protein A is comprised of the following (X)-(Z):

(X) Three helices (helix 1, helix 2, and helix 3 from the N-terminus)

(Y) Loop 1 which connects helix 1 and helix 2

(Z) Loop 2 which connects helix 2 and helix 3.

All of the amino acids directly involved in the binding with immunoglobulin are exposed to the surface of helix 1 and helix 2, and if these amino acids are replaced, then the binding specificities, etc. are likely to be changed.

On the other hand, it is known that the hydrophobic amino acids inside of the immunoglobulin binding domain do not directly make a contact with immunoglobulin and are not directly involved in binding specificity, but instead they do form hydrophobic bonding with other hydrophobic side chains which are spatially adjacent, significantly contributing to the stability of the three dimensional structure of the polypeptide.

It is supposed that the extent of the contribution generally correlates to a size of the side chain of a hydrophobic amino acid to some extent. It is also assumed that replacing an internal amino acid having a larger side chain with an amino acid having a smaller side chain can result in loss of hydrophobic bonding, and destabilize the native three dimensional structure of a polypeptide.

However, which position(s) of a hydrophobic amino acid(s) is(are) to be replaced with which amino acid(s) can not be easily determined in order to achieve the desired destabilization of the structure because the stability of the three dimensional structure of a polypeptide also depends on the characteristics of the individual polypeptide besides of the size(s) of the hydrophobic amino acid(s).

We have already investigated various replacements of hydrophobic amino acids having a small surface exposed area by amino acids having a smaller side chain in an immunoglobulin binding domain of Protein A, and revealed that mutants where a hydrophobic amino acid(s) around Loop 1 is replaced show the largest effects on the stability of the three dimensional structure of this domain (non-patent literature 3). However, this only suggests, to some extent, the correlation between an amino acid substitution and the stability of the three dimensional structure under a given condition of temperature (room temperature), and there is no description in relation to immunoglobulin.

On the other hand, if the three dimensional structure of Protein A is destabilized too much, a problem that its binding with immunoglobulin becomes difficult in the loading and washing steps, will arise in the first place. Therefore, the above studies could not be applicable to immunoglobulin purification as they are. That is, in order to purify immunoglobulin, it is required to be able to fully control the state where the three dimensional structure of a polypeptide for purification is stabilized, and the state where it is destabilized, by means of other than a pH change.

Note that a concept called the Gibbs free energy for denaturation is known as an indicator of the stability of the three dimensional structure of a polypeptide, and the descriptions about B domain of Protein A can be found in non-patent literatures 3 and 4.

[non-patent literature 1] Mol. Biotechnol. Vol. 10 (1998), P.9-16

[non-patent literature 2] J. Biotechnol. Vol. 76 (2000), P.233-244

[non-patent literature 3] Proc. Natl. Acad. Sci. USA Vol. 101 (2004), P.6952-6956

[non-patent literature 4] J. Mol. Biol. Vol. 372 (2007), P.254-267

SUMMARY OF THE INVENTION

As a result of intensive research to solve the above problems, we have found that certain Protein A mutants show a change in immunoglobulin binding properties by altering the three dimensional structure caused by a temperature change, etc., and moreover this can be achieved within a temperature range where the structure of immunoglobulin is not affected. Thus we have completed the present invention. The aim of the present invention is to develop a novel immunoglobulin binding polypeptide, the loss and formation of whose native three dimensional structure can be controlled under the conditions that the stability of the three dimensional structure of immunoglobulin to be purified is secured, and that any unwanted effects such as damage, the loss of functions, or unintended functions do not occur for immunoglobulin (pH 5-9, below 60° C.). Further, the aim of the present invention is to provide a novel purification method utilizing said polypeptide as a ligand immobilized to an affinity chromatography support, where a pH change and/or use of additives are not required, which is against the purpose of purification.

MEANS FOR SOLVING THE PROBLEM

The above aims are achieved by from the first invention to the 14th invention below.

The First Invention

A polypeptide, which is a mutant of the polypeptide of SEQ ID NO 1 or SEQ ID NO 2 wherein its immunoglobulin binding properties can be altered by changing temperature under the conditions of pH 5-9, below 60° C.

The Second Invention

The polypeptide according to the first invention, wherein the Gibbs free energy for the polypeptide fulfills at least any one of the following formulas (I) to (III):

$$\Delta\Delta G_{X\text{-}BWT} \leqq -3.3 \text{ kcal/mol} \quad \text{(I)}$$

$$\Delta\Delta G_{X\text{-}PWT} \leqq -4.2 \text{ kcal/mol} \quad \text{(II)}$$

$$\Delta\Delta G_{X\text{-}BGG} \leqq 4.2 \text{ kcal/mol} \quad \text{(III)}$$

(where $\Delta\Delta G_{X\text{-}BWT}$ represents $\Delta G_X-\Delta G_{BWT}$, i.e., the difference between the Gibbs free energy for denaturation of the polypeptide of the first invention, $\Delta G_X$, and the Gibbs free energy for denaturation of BWT (SEQ ID NO 1), $\Delta G_{BWT}$, under the conditions of 25° C., 1 atmosphere, and pH 5.5, $\Delta\Delta G_{X\text{-}PWT}$ represents $\Delta G_X-\Delta G_{PWT}$, i.e., the difference between the Gibbs free energy for denaturation for the polypeptide of the first invention, $\Delta G_X$, and the Gibbs free energy for denaturation for PWT (SEQ ID NO 2), $\Delta G_{PWT}$, under the conditions of 25° C., 1 atmosphere, and pH 5.5, $\Delta\Delta G_{X\text{-}BGG}$ represents $\Delta G_X-\Delta G_{BGG}$, i.e., the difference between the Gibbs free energy for denaturation for the polypeptide of the first invention, $\Delta G_X$, and the Gibbs free energy for denaturation for the polypeptide of SEQ ID NO 9, $\Delta G_{BGG}$, under the conditions of 25° C., 1 atmosphere, and pH 5.5.)

The Third Invention

The polypeptide according to the first invention or the second invention, wherein at least Leu at position 19 and/or Leu at position 22 in the polypeptide of SEQ ID NO 1 or SEQ ID NO 2 is replaced with Ala or Gly.

The Fourth Invention

The polypeptide according to any one of the first to the third inventions, which has 60% or more homology to the polypeptide of SEQ ID NO 1 or SEQ ID NO 2 in terms of an amino acid sequence.

The Fifth Invention

The polypeptide according to any one of the first to the fourth inventions, wherein an immunoglobulin binding ratio thereof at 0° C. to 10° C. is 30% or more of an immunoglobulin binding ratio of the polypeptide of SEQ ID NO 1 or SEQ ID NO 2.

The Sixth Invention

The polypeptide according to any one of the first to the fifth inventions, which is represented by any of SEQ ID NO 9, 10 to 21, and 46.

The Seventh Invention

A polypeptide which contains at least two ore more polypeptides according to any one of the first to the sixth inventions in one molecule.

The Eighth Invention

A Protein A mutant, which contains the polypeptide according to any one of the first to the seventh inventions in its molecule.

The Ninth Invention

An affinity chromatography material, which comprises at least one or more polypeptides selected from the polypeptide according to any one of the first to the seventh inventions or the Protein A mutant according to the eighth invention.

The Tenth Invention

A method for separating and/or purifying immunoglobulin using affinity chromatography, wherein the immunoglobulin is eluted by changing temperature.

The Eleventh Invention

The method for separating and/or purifying immunoglobulin according to the tenth invention, wherein the affinity chromatography material according to the ninth invention is used under the conditions of pH 5-9, below 60° C.

The Twelfth Invention

A gene which encodes a polypeptide selected from the polypeptide according to any one of the first to the seventh inventions or the Protein A mutant according to the eighth invention.

The Thirteenth Invention

A method for producing a Protein A mutant or a mutant of the immunoglobulin binding domain of Protein A for immunoglobulin purification, the method comprising the following steps of (1) and (2):

(1) A step of selecting the Protein A mutant or the mutant of the immunoglobulin binding domain of Protein A.

(2) A step of selecting those showing a change in immunoglobulin binding properties in response to a temperature change under the conditions of pH 5-9, below 60° C.

The Fourteenth Invention

A device for immunoglobulin purification comprising the following (M) and (N):

(M) An affinity chromatography column, wherein the affinity chromatography material according to the ninth invention is used.

(N) A means by which the temperature inside the column can be controlled and/or a means by which the temperature inside the column can be determined.

EFFECTS OF THE INVENTION

A polypeptide of the present invention is able to change its immunoglobulin binding properties by controlling the loss and formation of its native three dimensional structure, etc., under the conditions (pH 5-9, below 60° C.) that the stability of the three dimensional structure of an immunoglobulin (hereafter may be representatively referred to as "IgG") is secured, and that any unwanted effects such as damage, the loss of the functions, or unintended functions do not occur for immunoglobulin. Therefore, in the method for separating and/or purifying immunoglobulin of the present invention which uses these as a ligand in affinity chromatography, etc., all of the steps can be performed at neutral pH, and thus association/aggregation of immunoglobulin will not occur due to exposure to an acidic solution. For this reason, immunoglobulin which is not inactive can be easily collected with high purity. Further, the method for separation and/or purification of the present invention has an elution speed of immunoglobulin comparable to the conventional method which uses a pH change, and can be adequately used in industrial applications.

BEST MODE OF CARRYING OUT THE INVENTION

The Polypeptide of the Present Invention

The polypeptide of the present invention is a mutant of the polypeptide of SEQ ID NO 1 or SEQ ID NO 2, wherein its immunoglobulin binding properties can be altered by changing temperature under the conditions of pH 5-9, below 60° C.

The polypeptide of SEQ ID NO 1 used as a model system of the sequence of the polypeptide of the present invention represents a polypeptide which has the same amino acid sequence as B domain of Protein A from *Staphylococcus* (hereafter may be referred to as BWT, meaning the wild type B domain), and a polypeptide which has remarkably high specificity and affinity with a common region of immunoglobulin. In this polypeptide, the presence or absence of a carbohydrate chain, and the kind of a carbohydrate chain do not particularly matter. Further, the polypeptide of the present invention in itself may exist as a separate polypeptide, and other than that, as described below, it may exist as a part of another protein having said polypeptide as an immunoglobulin binding domain, including that it may exist as a part of "a polypeptide of the present invention which contains at least two or more mutants of the polypeptide of SEQ ID NO 1 or SEQ ID NO 2 in one molecule" or "a Protein A mutant" of the present invention, etc.

The polypeptide of SEQ ID NO 2 used as a model system of the sequence of the polypeptide of the present invention represents a polypeptide where position 29 in the polypeptide of SEQ ID NO 1 is replaced with Ala (hereafter may be referred to as PWT), and a polypeptide which has remarkably high specificity and affinity with a common region of immunoglobulin.

As used in the present invention, the term "mutant" means a polypeptide in which one or more mutations such as substitution, deletion, addition, or an insert, are introduced into the sequence of its parent polypeptide.

As used in the present invention, the phrase "immunoglobulin binding properties may change by temperature under the conditions of pH 5-9, below 60° C." means that under the condition of pH 5-9, below 60° C. where the three dimensional structure of immunoglobulin is not affected, "the strength of binding" to immunoglobulin and/or "specificity" for immunoglobulin, etc. may change by changing temperature, whereby allowing immunoglobulin to be purified. More specifically, for example, it means that immunoglobulin could be bound when loaded into a column packed with the polypeptide of the present invention followed by washing the column in a low temperature range, and then after bringing the temperature to a higher range, the immunoglobulin bound in the low temperature range could be released due to the change in the structure of itself (the polypeptide). Further specifically, it means that there is a difference in the immunoglobulin binding properties of the polypeptide between at a low temperature range, for example, 0-15° C., preferably 0-8° C., more preferably around 5° C., and a high temperature range, for example, 25-60° C., preferably 30-45° C., more preferably 32-38° C., in particular preferably around 35° C.

Note that the polypeptide of the present invention can bind/elute "human IgG," which has a high demand for purification among immunoglobulins, at around pH 7, while it is also capable of binding and releasing IgGs other than human under the conditions of pH 5-9, or in some cases pH 5.9-8.1.

In addition, it was found that a polypeptide of −0.5 kcal/mol$\leqq\Delta\Delta G_{X\text{-}BGG}\leqq$1.5 kcal/mol showed a rather improved recovery ratio by around 5 to 6% for "human IgG" at pH 8.0-8.4 (in particular around pH 8.2).

For the first time, use of such polypeptide enables immunoglobulin to be extracted while the pH of an experiment system is kept at neutral. Performing extraction/purification using a pH change has been, so to speak, a conventionally fundamental principle in the art. In order to avoid this, the present invention is innovative in terms of a viewpoint of using a polypeptide which changes its immunoglobulin binding properties by changing temperature instead of pH.

Whether a mutant changes its immunoglobulin binding properties or not by temperature can be easily confirmed by actually purifying immunoglobulin using the candidate mutant as a ligand for column chromatography, etc., where the mutant can be selected by, for example, using the indicators specifically described below.

A First Indicator: Difference in the Gibbs Free Energy for Denaturation

Indicators for a mutant whose "immunoglobulin binding properties may change by temperature under the conditions of pH 5-9, below 60° C.," preferably include the Gibbs free energy for denaturation of the mutant polypeptide fulfills at least any of the conditions of the following formulas (I) to (III), etc. $\Delta\Delta G_{X\text{-}BWT}$ is preferably in the range shown in formula (I)-1, more preferably in formula (I)-2, in particular preferably in formula (I)-3.

$$\Delta\Delta G_{X\text{-}BWT}\leqq -3.3\ \text{kcal/mol} \qquad \text{(I)-1}$$

$$-13.0\ \text{kcal/mol}\leqq\Delta\Delta G_{X\text{-}BWT}\leqq -5.6\ \text{kcal/mol} \qquad \text{(I)-2}$$

$$-11.7\ \text{kcal/mol}\leqq\Delta\Delta G_{X\text{-}BWT}\leqq -6.9\ \text{kcal/mol} \qquad \text{(I)-3}$$

The reason is that an immunoglobulin recovery ratio of no less than 10% can be achieved by formula (I)-1, no less than 30% by formula (I)-2, and no less than −55% by formula (I)-3.

$\Delta\Delta G_{X\text{-}BWT}$ is preferably in the range shown in formula (II)-1, more preferably in formula (II)-2, in particular preferably in formula (II)-3.

$$\Delta\Delta G_{X\text{-}BWT}\leqq -4.2\ \text{kcal/mol} \qquad \text{(II)-1}$$

$$-13.9\ \text{kcal/mol}\leqq\Delta\Delta G_{X\text{-}BWT}\leqq -6.5\ \text{kcal/mol} \qquad \text{(II)-2}$$

$$-12.6\ \text{kcal/mol}\leqq\Delta\Delta G_{X\text{-}BWT}\leqq -7.8\ \text{kcal/mol} \qquad \text{(II)-3}$$

The reason is that an immunoglobulin recovery ratio of no less than 10% can be achieved by formula (II)-1, no less than 30% by formula (II)-2, and no less than 55% by formula (II)-3.

$\Delta\Delta G_{X\text{-}BGG}$ is preferably in the range shown in formula (III)-1, more preferably in formula in particular preferably in formula $$\Delta\Delta G_{X\text{-}BGG} \leqq 4.2 \text{ kcal/mol} \quad \text{(III)-1}$$

$$-1 \text{ kcal/mol} \leqq \Delta\Delta G_{X\text{-}BGG} \leqq 1.5 \text{ kcal/mol} \quad \text{(III)-2}$$

$$-0.5 \text{ kcal/mol} \leqq \Delta\Delta G_{X\text{-}BGG} \leqq 1.5 \text{ kcal/mol} \quad \text{(III)-3}$$

The reason is that an immunoglobulin recovery ratio of no less than 38% can be achieved by formula (III)-1, no less than 70% by formula and no less than 72% by formula (III)-3.

(where, in formula (I), $\Delta\Delta G_{X\text{-}BWT}$ represents the difference between the Gibbs free energy for denaturation of a polypeptide of the present invention, $\Delta G_X$, and the Gibbs free energy for denaturation of BWT (SEQ ID NO 1), $\Delta G_{BWT}$, under the conditions of 25° C., 1 atmosphere, and pH 5.5, $\Delta\Delta G_{X\text{-}PWT}$ in (II) represents the difference between the Gibbs free energy for denaturation of a polypeptide of the present invention, $\Delta G_X$, and the Gibbs free energy for denaturation of PWT (SEQ ID NO 2), $\Delta G_{PWT}$, under the conditions of 25° C., 1 atmosphere, and pH 5.5, and $\Delta\Delta G_{X\text{-}BGG}$ in (III) represents the difference between the Gibbs free energy for denaturation of a polypeptide of the present invention, $\Delta G_X$, and the Gibbs free energy for denaturation of the polypeptide of SEQ ID NO 9, $\Delta G_{BGG}$, under the conditions of 25° C., 1 atmosphere, and pH 5.5.)

Gibbs Free Energy for Denaturation

As used in the present invention, the Gibbs free energy for denaturation means that the energy required for the reaction of polypeptide's transition from the native state to the denatured state, which is expressed using the difference of the Gibbs free energy for each of the native state and the denatured state, and it is designated as "ΔG of polypeptide X," or "$\Delta G_X$," etc. The larger this value is, the more energy is required for denaturation, i.e. meaning that the polypeptide is more difficult to be denatured. The Gibbs free energy can be used as an indicator which represents the thermodynamic state of a polypeptide under certain conditions. The stability of the three dimensional structure of said polypeptide X, i.e. the above $\Delta G_X$, representing the difficulty in the transition to the denatured state can be shown by $\Delta G_{J\text{-}I}=G_J-G_I=\Delta G_X$, where $\Delta G_{J\text{-}I}$ is the difference between the Gibbs free energy of the denatured state, $G_J$, and the Gibbs free energy of the native state, $G_I$.

In the present invention, $\Delta\Delta G_{X\text{-}BWT}$, $\Delta\Delta G_{X\text{-}PWT}$, $\Delta\Delta G_{X\text{-}BGG}$, in which $\Delta G_X$ of each of the mutants of the present invention is further compared with ΔG of SEQ ID NO 1 (BWT), SEQ ID NO 2 (PWT), or SEQ ID NO 9 (BGG) respectively, are used as indicators for a mutant suitable for recovering immunoglobulin.

It is known that a protein molecule, in particular a small protein molecule of 100 or less amino acids, biologically functions with the equilibrium maintained between the native state and the denatured state. In particular, it is known that B domain of Protein A and many of its mutants reversibly undergo the transition between the native state and the denatured state without forming a stable intermediate. In that case, the stability of the three dimensional structure of Protein A can be scored using the difference in the Gibbs free energy of the native state and the denatured state (ΔG). Moreover, "the difference in the stability of the three dimensional structure between certain mutants" can be evaluated by the difference between each ΔG (hereafter referred to as ΔΔG).

For example, the value of ΔG for the denaturation of the Y14W mutant of B domain (a mutant with Y at position 14 replaced by W) has been reported to be $\Delta G_{Y14W}$=5.0 kcal/mol (25° C., 1 atmosphere, pH 5.5) (see "Result," etc., p. 6953 in non-patent literature 3).

(In this regard, "Y14W" in the present invention is designated as "Y15W" in non-patent literature 3 and non-patent literature 4. This is due to a different view of the starting position of the polypeptide. The way of recognizing which position of amino acids "B domain" in Protein A starts and ends at is somewhat different from person to person. Since B domain in non-patent literature 3 and 4 was defined from the amino acid (T) which is at one position upstream relative to the N-terminal amino acid (A) in B domain of the present invention, the number representing the mutated position is greater by one compared to the present invention. Note that the difference in the N terminus of B domain (the number of amino acids of the polypeptides differs by one) is not required to be considered in calculating the Gibbs free energy. The reason is that since the value of Gibbs free energy is dictated by a three dimensional structure, the N terminus which is less involved in the formation of the three dimensional structure hardly affects the value.

Therefore, if the value of ΔG for a further mutant A based on the Y14W is $\Delta G_A$=4.0 kcal/mol under the same conditions, the value where $G_{Y14W}$ is subtracted from $\Delta G_A$ ($\Delta\Delta G_{A\text{-}Y14W}$) will be −1.0 kcal/mol, and one can evaluate that the three dimensional structure of the mutant A is more unstable than that of the Y14W mutant by 1.0 kcal/mol.

Likewise, if the value of ΔG for another mutant B based on the Y14W is $\Delta G_B$=6.0 kcal/mol under the same conditions, $\Delta\Delta G_{B\text{-}Y14W}$ will be +1.0 kcal/mol, indicating that the three dimensional structure of the mutant B is more stable than that of the Y14W mutant by 1.0 kcal/mol.

Determination of the Gibbs Free Energy for Denaturation

The values of ΔG for Protein A and its mutants of the present invention can be determined by a known experimental approach using the ultra-sensitive differential scanning calorimetry (DSC), etc. (Fersht, A., Structure and Mechanism in Protein Science: A Guide to Enzyme Catalysis and Protein Folding, W. H. Freeman and Company, New York), and MG can be calculated from the values. Alternatively, MG can be also calculated by using previously reported values of ΔG for the B domain mutants of Protein A, etc. (non-patent literatures 3 and 4).

In short, the reason is that while ΔGs in the case that mutations such as F30G (F at position 30 being replaced by G) are introduced are shown in non-patent literature 3, non-patent literature 4 suggests that the effects on ΔG for a mutant can be computed by addition of each ΔG due to various mutants.

For this reason, the values of ΔΔG can be computed between the polypeptides to be compared by the addition of ΔGs for different mutations.

A Method for Calculating $\Delta\Delta G_{X\text{-}PWT}$ in (II)

Specifically, $\Delta\Delta G_{X\text{-}PWT}$ in formula (II) of the present invention can be computed using the values represented by $\Delta G_{D\text{-}N}$ listed in Table 4 at page 262 of non-patent literature 4 according to the above idea that "a value of ΔΔG can be computed between polypeptides to be compared by addition of ΔGs for different mutations" ($G_{D\text{-}N}$ in Table 4).

In this regard, in order to use $\Delta G_{D\text{-}N}$ in Table 4, the values in this Table 4 requires attention in terms of the following two points.

Note 1

In order to compute $\Delta G_{D-N}$ of each "mutant itself," it is necessary to subtract $\Delta G_{D-N}$ for "the Y15W mutant" (which is also a value for the Y15W mutant itself. the value in the top of Table 4 (4.99)) from $\Delta G_{D-N}$ shown in Table 4 of non-patent literature 4. It is because the values of $\Delta G_{D-N}$ in Table 4 are those for "the Y15W mutant" which is a polypeptide corresponding to B domain of Protein A and "various mutants (all) into which a further mutation is introduced in addition to Y15W."

Note 2

When using Table 4, it is necessary to use the numbering where "1" is added to a number indicating a mutated position of the present invention (for example, for L19A of the present invention, the value of L20A in Table 4 is to be used). It is because the starting position of B domain is differently recognized between non-patent literature 4 and the present invention as mentioned above.

Specific Examples for Calculation

A specific method for calculating $\Delta\Delta G$ is to be illustrated based on the above notes 1 and 2.

A Case of One Amino Acid Mutation

For example, the only difference in amino acid mutations between Example 12 (BGG14) described below and PWT is that L at position 19 in PWT is G in BGG14.

Therefore, $\Delta\Delta G_{X-PWT}$ for BGG14 can be calculated as follows:

$$\Delta\Delta G_{BGG14-PWT} = \Delta G_{D-N} \text{ for the } L20G$$
$$(L19G \text{ in the present invention})$$
$$\text{mutant itself}$$
$$= \text{The value for } L20G \ (0.78) -$$
$$\text{the value for } Y15W \ (4.99) \text{ in Table 4}$$
$$\approx -4.2$$

A Case of Multiple Amino Acid Mutations

As mentioned above, a value of $\Delta\Delta G_{X-PWT}$ can be calculated by addition of "$\Delta G$ for an amino acid mutation itself" between mutant X and mutant PWT.

For example, the only difference in amino acid mutations between the mutant in Example 11 (BGG13) and PWT is that L at position 19 in PWT is G in BGG13, and L at position 22 in PWT is A in BGG13 (a mutation is introduced into two positions).

Therefore, $\Delta\Delta G_{X-PWT}$ for BGG13 can be calculated as follows:

$$\Delta\Delta G_{BGG13-PWT} = \{\Delta G_{D-N} \text{ for the } L20G \ (L19G \text{ in the present invention}) \text{ mutant itself}\} +$$
$$\{\Delta G_{D-N} \text{ for the } L23A \ (L22A \text{ in the present invention}) \text{ mutant itself}\}$$
$$= \{\text{the value for } L20G \ (0.78) - \text{the value for } Y15W \ (4.99) \text{ in Table 4}\} +$$
$$\{\text{the value for } L23A \ (-0.01) - \text{the value for } Y15W \ (4.99) \text{ in Table 4}\}$$
$$= (0.78 - 4.99) + (-0.01 - 4.99)$$
$$\approx -9.2$$

Note that Formula (II) is derived as a range of $\Delta\Delta G_{X-PWT}$ from Examples descried below where a certain IgG recovery ratio (a purification yield) is achieved.

A Method for Calculating $\Delta\Delta G_{X-PWT}$ in (I)

It is known that in a helix-forming small polypeptide such as B domain and Z domain, a mutation where Ala located around the central region of a helix is replaced by Gly decreases $\Delta G$ (the Gibbs free energy for denaturation) for such polypeptide by about 0.9 kcal/mol, i.e. destabilizing its three dimensional structure by such amount (Fersht, A., Structure and mechanism in protein science: A guide to enzyme catalysis and protein folding. W. H. Freeman and Company, New York (1998), Table 17.3, p528). Therefore, this can be rephrased as SEQ ID NO 1 having a lower Gibbs free energy for denaturation by 0.9 kcal/mol relative to SEQ ID NO 2.

Formula (I) is a range derived according to this by calculation based on formula (II).

A Method for Calculating $\Delta\Delta G_{X-BGG}$ in (III)

With regard to formula (III), for a mutant which contains, for example, a substitution of Leu at position 22 by Gly, the Gibbs free energy for denaturation can not accurately determined since the three dimensional structure is highly destabilized, and thus formula (I) and (II) can not be computed. Therefore, for that case, a relative difference in the Gibbs free energy for denaturation was obtained using the polypeptide of SEQ ID NO 9 (BGG in Example 5) as a reference, which was first confirmed to show a high immunoglobulin recovery ratio by temperature difference, and formula (III) was defined as the range where an immunoglobulin recovery ratio was found high. Note that this difference was computed in a similar manner as (II) from the values found in non-patent literature 3 and 4, etc.

For example, the only difference in amino acid mutations between the mutant in Example 9 (BGG11) and BGG is that G at position 19 of BGG is A in BGG14. Here, a value for G20A (G19A in the present case) is not directly found in Table 4, and for this case, it can still be computed by subtracting the value for L20G mutation from the value for the L20A mutation.

Therefore, $\Delta\Delta G_{X-BGG}$ for BGG11 can be calculated as follows:

$$
\begin{aligned}
\Delta\Delta G_{BGG11-BGG} &= \Delta G_{D-N} \text{ for the } G20A \\
&\quad (G19A \text{ in the present invention}) \\
&\quad \text{mutant itself} \\
&= \{\Delta G_{D-N} \text{ for the } L20A\ (L19A \text{ in the present invention}) \text{ mutant itself}\} - \\
&\quad \{\Delta G_{D-N} \text{ for the } L20G\ (L19G \text{ in the present invention}) \text{ mutant itself}\} \\
&= (\text{the value for } L20A - \text{the value for } Y15W \text{ in Table 4}) - \\
&\quad (\text{the value for } L20G - \text{the value for } Y15W \text{ in Table 4}) \\
&= (2.32 - 4.99) - (0.78 - 4.99) \\
&= 2.32 - 0.78 \\
&\approx 1.5
\end{aligned}
$$

For example, the only difference in amino acid mutations between the mutant in Example 10 (BGG12) described below and BGG is that G at position 19 in BGG is L in BGG14.

Here, a value for G20L (G19L in the present case) is not directly found in Table 4, and for this case, it can still be computed by subtracting the value for L20G mutation from the value for the L20L mutation.

Note that the value for L20L, which is not presented in Table 4, will be 0 since L20L means no mutation.

Therefore, $\Delta\Delta G_{X\text{-}BGG}$ for BGG12 can be calculated as follows:

$$
\begin{aligned}
\Delta\Delta G_{BGG12-BGG} &= \Delta G_{D-N} \text{ for the } G20L \\
&\quad (G19L \text{ in the present invention}) \\
&\quad \text{mutant itself} \\
&= \{\Delta G_{D-N} \text{ for the } L20L\ (L19L \text{ in the present invention}) \text{ mutant itself}\} - \\
&\quad \{\Delta G_{D-N} \text{ for the } L20G\ (L19G \text{ in the present invention}) \text{ mutant itself}\} \\
&= 0 - (\text{the value for } L20G - \text{the value for } Y15W \text{ in Table 4}) \\
&= 0 - (0.78 - 4.99) \\
&= +4.2
\end{aligned}
$$

For information, even for a polypeptide mutant designed based on SEQ ID NO 1 (BWT), it is not necessarily required to be evaluated by formula (I) using $\Delta\Delta G_{X\text{-}BWT}$, the Gibbs free energy for denaturation of SEQ ID NO 1. All of each polypeptide of the present invention may be evaluated by any of formula (I) to (III).

A Second Indicator: Amino Acid Arrangements

A Polypeptide of the Present Invention in which at Least Leu at Position 19 and/or Leu at Position 22 in the Polypeptide of SEQ ID NO 1 or SEQ ID NO 2 is Replaced with Ala or Gly From a different point of view other than the Gibbs free energy for denaturation, indicators for obtaining a mutant whose "immunoglobulin binding properties may change by temperature under the conditions of pH 5-9, below 60° C.," include the conditions of "a mutant of the polypeptide of SEQ ID NO 1 or SEQ ID NO 2, wherein at least Leu at position 19 and/or Leu at position 22 is replaced with Ala or Gly."

Specific "mutants of the polypeptide of SEQ ID NO 1 or SEQ ID NO 2, wherein at least Leu at position 19 and/or Leu at position 22 is replaced with Ala or Gly" include not only 16 mutants of the polypeptide of SEQ ID NO 1 or SEQ ID NO 2 in which at least Leu at position 19 and/or Leu at position 22 is replaced with Ala or Gly but also mutants into which a further substitution, deletion, addition, or insertion at a different amino acid(s) is (are) introduced without changing such mutations.

The replacement of Leu at position 19 and/or Leu at position 22 with Ala or Gly is contemplated such that the three dimensional structure the polypeptide of SEQ ID NO 1 or 2 can be altered due to a temperature change by decreasing the stability of the three dimensional structure of it.

Mutations other than those at position 19 and 22 include, for example, a mutation where a hydrophobic amino acid inside the protein is mutated to another hydrophobic amino acid as well as a mutation where a hydrogen bond by a side chain is deleted.

Mutations where a hydrogen bond is deleted include a substitution of Gln (in particular, exposed to the protein surface, for example, Gln at position 26) to Gly. If the amide group on the side chain of Gln is involved in the hydrogen bond, the three dimensional structure of the polypeptide is thought to be destabilized when the amide group is deleted, and the hydrogen bond is lost. One example of such mutations is BLG28 in Example 17, etc. described below.

Further, even for a hydrophilic amino acid, if it has a side chain with a significantly hydrophobic moiety, a mutation to delete such moiety can decrease the stability of the three dimensional structure of a protein. For example, when Arg, which is hydrophilic and carries a charge in a neutral solution, is replaced by an amino acid which does not have a strongly hydrophobic methylene group (or has a less amount of a methylene group), for example, such as Gly, the native three dimensional structure of that polypeptide tends to become unstable.

Examples of such mutations include Example 18 described below, etc.

In this regard, it is required for these mutants to be able to change their immunoglobulin binding properties in response to a temperature change in the pH range of 5-9.

For this temperature change, a difference of preferably 5° C. or more, more preferably 10° C. or more, or even more preferably 20° C. or more is preferred because controlling temperature becomes easy in purifying Immunoglobulin.

A Third Indicator: Homology in Polypeptides

A Polypeptide of the Present Invention Having 60% or More Homology with the Polypeptide of SEQ ID NO 1 or SEQ ID NO 2

A mutant of the present invention preferably has a certain level of homology with the polypeptide of SEQ ID NO 1 or SEQ ID NO 2 in terms of an amino acid sequence. It is because B domain represented by SEQ ID NO 1 (SEQ ID NO 2 is a one-amino-acid-substituted version of this) has shown proven binding properties with immunoglobulin.

However, it should be understood that this is merely a indicator in the present invention to obtain a mutant retaining binding properties with immunoglobulin, and excluding those having a low homology with SEQ ID NO 1 and/or SEQ ID NO 2 is not intended.

Homology means being similar in terms of an amino acid sequence, for example, it is preferred that 60% or more, more preferably 70% or more, even more preferably 80% or more, in particular preferably 90% or more of the amino acid sequences are identical.

Even non-identical amino acid may be preferred because binding properties with immunoglobulin is likely retained if a substitution is made between amino acids with a similar chemical property and/or a structural similarity.

Such substitution of an amino acid with a similar chemical property and/or a structural similarity, i.e. a specific aspect of amino acid substitutions of highly conserved amino acids is known, and namely exemplified in the followings:

Glycines (Gly) may be preferably substituted with proline (Pro), alanine (Ala), and a valine (Val), Leucine (Leu) may be preferably substituted with isoleucine (Ile), Glutamic acid (Glu) may be preferably substituted with glutamine (Gln), Aspartic acid (Asp) may be preferably substituted with asparagine (Asn), Cysteine (Cys) may be preferably substituted with threonine (Thr), Thr may be preferably substituted with serine (Ser) and Ala, Lysine (Lys) may be preferably substituted with arginine (Arg).

Note that a combination of amino acids with a similar chemical property and/or a structural similarity is not necessarily limited to these.

A Fourth Index: Binding Properties with Immunoglobulin

A Polypeptide of the Present Invention Having 30% or More of an Immunoglobulin Binding Ratio of the Polypeptide of SEQ ID NO 1 or SEQ ID NO 2

It is preferred that a mutant of the present invention is equivalent to the polypeptide of SEQ ID NO 1 or SEQ ID NO 2 in terms of an immunoglobulin binding ratio at 0 to 15° C. "Being equivalent" means that it is preferred to have, for example, 30% or more of the immunoglobulin binding ratio of the parent polypeptide, and to have more preferably 40% or more, even more preferably 50% or more, in particular preferably 70% or more of the binding ratio.

Note that these immunoglobulin binding ratios can be determined by actually filling a column, etc. with supports in which such a mutant is used as a ligand, running the column with a solution containing immunoglobulin, and measuring the amount of immunoglobulin bound to the ligand and the amount of immunoglobulin running through the column without binding.

The amount of immunoglobulin bound to the ligand can be measured by eluting immunoglobulin by changing pH and/or temperature.

Because, for example, the immunoglobulin binding domains (E, D, A, C domains) of Protein A, and Z domain which is a known mutant of B domain, are intrinsically highly homologous with B domain, a mutant where at least Leu in these polypeptides corresponding to position 19 and/or position 22 are replaced with Ala or Gly is also included in the polypeptides of the present invention.

As for a polypeptide of the present invention, those in which Leu at position 19 and/or Leu at position 22 in B domain are mutated to Ala or Gly, and Gly at position 29 is further mutated to Ala are preferred, and in particular, those shown in Examples are preferred.

Note that such mutated polypeptides can also be created from the genes of other immunoglobulin binding domains having homology with B domain, and its origin does not matter.

For example, a similar mutated polypeptide can be created by mutating the gene for Z domain such that Val at position 1 in Z domain is mutated to Ala, and Leu at position 19 and/or Leu at position 22 in Z domain are mutated to Ala or Gly because Z domain in which position 1 and position 29 of B domain are replaced with Val and Ala respectively is considerably similar to B domain in sequence.

Note that an alkaline resistance can be improved for the above polypeptides of the present invention by introducing a mutation(s) described in US2005/14356A1 to the polypeptides in addition to the above various mutations.

Specifically, an alkaline resistance can be improved by mutating at least one Asn in the polypeptide of SEQ ID NO 1 or SEQ ID NO 2 to the other amino acids in addition to the above various mutations.

From the viewpoint that the polypeptide of the present invention is to be used for immunoglobulin purification at neutral pH, an alkaline resistance is not required in particular. However, alkaline washing between purification cycles may be performed to completely remove possible contaminants attached to the polypeptide when repeatedly used in the purification process.

As for the other amino acids to which Asn may be mutated, uncharged amino acids are preferred, for example, Thr, Gln, Ala, Ser, and so on, and Thr is in particular preferred.

It is known, from the above literature, that the decrease in an alkali resistance can be caused mainly by Asn being converted into negatively charged Asp by the alkalies.

The Asn candidates for the above substitutions include Asn at positions 3, 6, 11, 21, 23, 28, 43, and 52 in the various polypeptides of the present invention, and one or more of these Asn may be mutated to other amino acids as described above. In particular, substitution of Asn at position 23 is preferred since it is known from the above literature (US2005/14356A1) that a mutation at position 23 resulted in a significantly increased alkaline resistance.

Immunoglobulin to be Purified in the Present Invention

In the present invention, immunoglobulin to be purified may be those from the body of an animal, or cultured animal cells as well as those artificially synthesized to mimic these structures, and may be a polyclonal antibody or a monoclonal antibody.

Such an animal may be human as well as a non-human animal such as mouse, rat, rabbit, swine, equine, canine, and feline, and such immunoglobulin may be such that immunoglobulin from a non-human animal is converted into a chimera such as a humanized, or a human type (completely humane) using a biotechnological approach, etc.

Immunoglobulins to be purified also include a so-called phage antibody which is only comprised of a VH chain, a heavy chain variable region of a monoclonal antibody, and a VL chain, a light chain variable region.

The present invention can be most useful for purifying humanized or human IgG.

A Method for Producing a Polypeptide of the Present Invention

A polypeptide of the present invention can be chemically or enzymatically synthesized from scratch using a polypeptide synthesizing apparatus according to conventional methods, or first a corresponding gene can be created, then followed by expressing it using the gene. Then the gene for a mutated polypeptide can be prepared using known genetic recombinant techniques as described below in "a method for preparing a gene of the present invention". A polypeptide of the present invention can be economically produced in large amounts by transforming a host cell with a vector containing DNA corresponding to the amino acid sequence of the polypeptide of the present invention, and culturing the host.

DNA corresponding to the amino acid sequence of the polypeptide of the present invention can be completed by preparing synthetic oligonucleotides having tens of bases which are partially overlapped, and then applying the polymerase chain reaction (PCR) method, etc. to them. Alternatively DNA corresponding to the amino acid sequence of the polypeptide of the present invention can be completed by introducing an amino acid mutation into a desired position using, as a primer for PCR, synthetic oligonucleotides into which a mismatched base pair is incorporated, and using, as a template, DNA (including a plasmid DNA) corresponding to an amino acid sequence of the naturally occurring polypeptide created in a similar manner.

DNA corresponding to the amino acid sequence of the polypeptide of the present invention is to be inserted in an expression vector. For an expression vector, a commercially available plasmid vector can be used including, but not limited to, for example, a pET vector system (Merck, Japan) and/or a pRSET vector system (Invitrogen, Japan), which are preferred because they are widely used and can express a large amount of polypeptide in combination with a host *E. coli.*

Recognition sequences of several kinds of DNA restriction enzymes are incorporated into the cloning site of the expression vectors, and the expression vectors can be cut at a given position by using a specific restriction enzyme. For example, restriction enzymes such as BamHI and Ndel are commercially available (from NEB etc.). Commercial T4 DNA ligase (from NEB, etc.) can be used in order to ligate DNA corresponding to an amino acid sequence of a polypeptide of the present invention into the digested site.

Appropriate combination of an expression vector and a host cell is important for use, and, for example, it is preferred to use bacterial cells such as *E. coli* BL21 (DE3) and C41 (DE3) as a host cell for a pET vector system and a pRSET vector system. They have been already used to express the domains of Protein A, and there is also a track record for large scale expression of Protein A in combination with the above-mentioned vectors.

Use of pET15b plasmid (Merck, Japan) in which the His tag gene is already incorporated as a fusion tag, and/or pET-41a-c (+) or pET-42a-c(+) plasmid (both are from Merck, Japan) in which the GST tag gene is incorporated are preferred because it is convenient to purify a polypeptide of the present invention.

In order to introduce an expression vector to transform a host cell, the heat shock method can be used, in which a mixed solution of expression vectors and host cells is treated at about 42° C. for tens of seconds. In addition, the electroporation method is similarly preferred, in which an electric pulse is applied to the mixed solution.

A transformed host cell into which an expression vector containing DNA encoding a polypeptide of the present invention is introduced, can be cultured using suitable media by the conventional methods. For example, when a host cell is *E. coli*, liquid media such as LB medium (Luris-Bertani medium) or 2×TY medium are preferred.

Culture is usually performed at between 15° C. and 40° C., and between 30° C. and 37° C. is particularly preferred. It is preferred to shake or agitate the medium optionally with aeration and pH adjustment as necessary. Induction of polypeptide expression can be performed by adding isopropyl-1-β-D-galactopyranoside (IPTG) etc. to the medium.

The host cells expressing a polypeptide of the present invention are separated from the medium by centrifugation or filtration. These host cells are suspended to a suitable buffer solution to perform cell lysis. The freeze-thawing method can be used for cell lysis in which freezing and thawing are repeated several times, but in order to lyse the host cells more efficiently, it is preferred to perform sonication or pressure treatment. By further performing centrifugation after cell lysis, the polypeptide of the present invention can be collected in a soluble fraction.

A Polypeptide of the Present Invention Containing at Least Two or More Mutants of the Polypeptide of SEQ ID NO 1 or SEQ ID NO 2 in One Molecule A polypeptide of the present invention containing at least two or more "mutants of the polypeptide of SEQ ID NO 1 or SEQ ID NO 2" (hereafter may be referred to as "GG") in one molecule is a polypeptide characterized in that at least two or more polypeptides of the present invention described above are included as immunoglobulin binding domains. Specific examples include:

A polypeptide containing two "GGs" (hereafter may be referred to as "2GG containing polypeptide")

A polypeptide containing three "GGs" (hereafter may be referred to as "3GG containing polypeptide"), A polypeptide containing four "GGs" (hereafter may be referred to as "4GG containing polypeptide") and so forth.

Hereafter, these may be collectively called as an "nGG containing polypeptide" (a polypeptide which contains the number n of GGs in one molecule: n is an integer greater than 1).

There is no particular upper limit for the number n, but when used as a ligand for affinity chromatography, it is preferred that the number n of "GGs" is no greater than six, further preferably no greater than 5, particularly preferably no greater than 4, considering its compatibility with the size and/or kind etc. of affinity chromatography supports and/or affinity chromatography columns.

In addition, there are a number of "GGs" which are mutants of the present invention. These "GGs" contained in one molecule are not necessarily the same kind of "GG", and they may be different kinds of "GGs." However, it is preferred to choose "GGs" having a similar "tendency of the change in immunoglobulin binding properties at pH 5-9 below 60° C." in order to improve effectiveness of immunoglobulin separation/purification.

Note that the "nGG containing polypeptide" may contain amino acids for connecting "GGs", and other amino acids other than "GGs" themselves. "A polypeptide of the present invention containing at least two or more mutants of the polypeptide of SEQ ID NO 1 or SEQ ID NO 2 in one molecule" can be produced by preparing a gene encoding the "nGG containing polypeptide" in advance and then inserting it into a plasmid vector, or it can be relatively easily produced, for example, according to the followings.

For example, a "2GG containing polypeptide" of the present invention can be produced by introducing an additional gene for the "GG" polypeptide into the downstream of the existing "GG" gene in the plasmid vector used for producing the polypeptide "GG" of the present invention as described above. Upon introduction, a combination is to be selected from the multiple restriction enzyme recognition sites incorporated into the plasmid such that the already introduced polypeptide gene will not be removed off.

A "3GG containing polypeptide" of the present invention can be produced by, for example, introducing a "2GG containing polypeptide" gene into the plasmid vector used for producing the polypeptide "GG" of the present invention as described above. A "2GG containing polypeptide" gene can be obtained from the plasmid used for producing a "2GG containing polypeptide," and when doing this, the restriction enzyme cutting sites at the both ends of the "2GG containing polypeptide" gene can also be designed as desired by amplifying it using suitable primers by the PCR method, etc.

Other "nGG containing polypeptides" of the present invention can be easily produced in the similar manner as described above.

Note that when producing an "nGG containing polypeptide, a "(n−1) GG containing polypeptide" may be digested upon introduction if a combination of restriction sites is such that the region connecting "GGs" each other in the "(n−1) GG containing polypeptide" gene to be inserted is recognized by the same restriction enzyme which recognizes the restriction site in the plasmid for producing "GG". Therefore, in this case, it is preferred to treat a restriction enzyme recognition site which is present in the "GG" connecting region in the "(n−1) GG containing polypeptide" such that it may not be cut between "GGs" upon plasmid digestion by modifying the site using site directed mutagenesis etc.

Modification of the recognition site for XhoI using site directed mutagenesis can also be achieved by inserting a DNA sequence corresponding to one amino acid such as Ser or Ala into the recognition site for XhoI. In this case, a fusion polypeptide in which one amino acid such as Ser or Ala is inserted into at least one of the connection sites between polypeptides will be produced.

A Protein A Mutant of the Present Invention

A Protein A mutant of the present invention is a mutant of Protein A which contains a polypeptide of the present invention as described above in the molecule. This can be carried out using the Protein A gene by a known mutagenesis method such as site directed mutagenesis, while it is also possible to use a method in which a gene for the immunoglobulin binding domain in the Protein A gene is converted into a polypeptide gene of the present invention or an "nGG containing polypeptide" gene corresponding to it using homologous recombination to express the protein.

Purification of a Polypeptide of the Present Invention ("GG", an "nGG Containing Polypeptide") and a Protein A Mutant Any known purification methods, for example, such as a combination of salting-out and ion exchange chromatography, can be used to purify a polypeptide of the present invention ("GG", an "nGG polypeptide") and a Protein A mutant, etc. (hereafter may be collectively referred to as "a polypeptide (of the present invention), etc.") from a soluble fraction. "A polypeptide of the present invention, etc." is precipitated by adding ammonium salts, etc. to a soluble fraction, and then the precipitated "polypeptide of the present invention, etc." is collected by centrifugation followed by re-dissolving it in a suitable buffer. At this stage, the "polypeptide of the present invention, etc." would be 70% to 80% pure. Then, cation exchange chromatography and/or anion exchange chromatography can bring the purity of the "polypeptide of the present invention, etc." to 95% or more. For cation chromatography and cation chromatography, commercially available supports such as Resource S and Resource Q (GE health care bioscience, Japan) can be used respectively.

In addition, purification can be performed by introducing a tag gene into a gene portion corresponding to the N and/or C terminus of "a polypeptide of the present invention, etc." depending on the purpose, and then expressing it followed by purifying it using the expressed tag as an indicator.

Such tags include, for example, a tag comprising two to six histidines (hereafter may be referred to as a His tag or 6×His), a tag (GST) tag comprising glutathione-S-transferase, a maltose binding polypeptide (MBP) tag, a calmodulin, a Myc-tag (c-myc tag), a FLAG-tag, or known tags such as green fluorescence protein (GFP), and among these, a His tag and a GST tag, etc. are particularly preferred.

A His tag is most preferred because it has low immunogenicity due to its small size, and thus can be used for immunoglobulin purification without being removed from the purified "polypeptide of the present invention, etc.," and because it can be placed at either the N- or C-terminus of the "polypeptide of the present invention, etc.," and because many plasmids with a His tag pre-introduced are already in the market and readily available.

Methods for introducing a tag include a method in which a plasmid with a His tag gene and/or a GST tag gene preincorporated as a fusion tag as described above is used.

A polypeptide into which a tag is introduced can be purified by a known method appropriate for each tag. For example, in the case of a His tag, metal chelate affinity chromatography can be used, and for a GST tag, a purification method using glutathione-coupled affinity resin can be used. For metal chelate affinity chromatography, commercially available supports such as Ni-NTA (QIAGEN, Japan), which is a nickel-charged agarose gel, can be used.

A polypeptide with a fused tag can be used as it is, or the tag may be removed as necessary after purification. Thrombin and/or enterokinase, etc. can be used to remove the tags. Therefore, if removal of a tag is planned after purification, it is preferred to use a plasmid such as a pET15b plasmid (Merck, Japan), into which recognition sites for thrombin, etc. are already introduced.

An Affinity Chromatography Material of the Present Invention

Affinity chromatography materials of the present invention include a ligand comprising "a polypeptide of the present invention, etc.," an affinity chromatography support having said ligands, an affinity chromatography column containing said supports.

A Ligand of the Present Invention

"A polypeptide of the present invention, etc." can be used as a ligand for affinity chromatography, etc. as it is. A higher purity of the ligand themselves is preferred, for example preferably no less than 95% pure, even more preferably no less than 99% pure to improve a purification efficiency of immunoglobulin by affinity chromatography.

Affinity Chromatography Supports of the Present Invention

An affinity chromatography ligand of the present invention can be used in affinity chromatography as an affinity chromatography support by immobilizing it to a suitable support known in the art. Such supports include insoluble supports such as a plate; a test tube; a tube; a ball; a polymer or glass bead; matrix such as gel; a filter membrane comprised of polymers; and a membrane. As for the material, many kinds of materials such as agarose, polyacrylamide, dextran, and other macromolecular polymers are commercially available, and any solid supports of these can be used.

A Method for Immobilizing a Ligand of the Present Invention to a Support

Any of the various methods which are well known in the art and described in literature can be used for a method to immobilize an affinity chromatography ligand of the present invention to a solid support for affinity chromatography (refer to Japanese Unexamined Patent Publication (Kokai) No. 2006-304633 and PCT/SE03/00475 for detail). For example, the methods preferably include immobilization by activating solid supports with a coupling agent such as N-hydroxysuccinimide, or with a carboxyl group or a thiol group.

Note that a ligand may contain multiple kinds of polypeptides as the above polypeptides of the present invention if they are selected from those with similar immunoglobulin binding properties which can be altered by changing temperature under the conditions of pH 5-9 below 60° C. However, it is preferred to use a ligand predominantly containing a single kind of "GG" to improve and stabilize the effectiveness of separation and purification of immunoglobulin.

A ligand predominantly containing a single kind of "GG" means, for example, (1), (2) below, or "a combination of (1) with (2) containing the same kind of "GG" as in (1).

(1) A ligand containing a "GG"

(2) A ligand comprising a polypeptide predominantly containing the same kind of multiple "GGs" (an nGG containing polypeptide)

An Affinity Chromatography Column of the Present Invention

An affinity chromatography column of the present invention can be prepared by using the affinity chromatography supports of the present invention described above as at least a part of affinity chromatography supports to be filled.

A Method of the Present Invention for Separating and/or Purifying Immunoglobulin A method of the present invention for separating and/or purifying immunoglobulin is a method of eluting immunoglobulin by changing temperature under the conditions of pH 5.-9 below 60° C. using affinity chromatography.

Temperature Control

In a method of the present invention, it is important to control temperature. The methods of controlling temperature include, for example, a method of controlling the temperature inside an affinity chromatography column by providing a circulation jacket around the column such that circulating water or the like in the jacket directly contacts with the column, and controlling the temperature of circulating water or the like.

The temperature inside a column can be certainly checked by a measurement using a micro thermometer such as a temperature sensor, which is integrated inside the column. Alternatively, it is also possible to measure the temperature of eluted solutions from the column immediately after elution.

First, by regulating the temperature of heat media, such as water, circulating in the jacket to 0-15° C., preferably 0-10° C., more preferably at 5° C., the temperature inside the column will be set to such temperature. Then a sample solution containing immunoglobulin is injected into the column equilibrated with a suitable buffer at neutral pH, followed by completely removing substances unbound to the column using a wash buffer (neutral pH). It is also preferred to maintain the temperature of the equilibration buffer, the sample solution to be injected, and the wash buffer at a target temperature.

As described above, the immunoglobulin bound to the affinity ligand can be collected by changing and then maintaining the temperature inside the column at 30-45° C., preferably at 32-38° C., more preferably around 37° C., followed by running the column with a neutral elution buffer maintained at the same temperature.

This temperature of 37° C. is a temperature corresponding to the body temperature of an animal from which immunoglobulin originates, particularly to that of human, which is industrially most useful, and it is a temperature at which immunoglobulin is stable and biologically functions. In addition, in the separation and/or purification of the present invention, immunoglobulin can be separated and/or purified under the same neutral conditions as in blood, and therefore association/aggregation/inactivation of immunoglobulin is no longer an issue, and furthermore immunoglobulin can be collected with causing no or little damages on its native functions including known and unknown functions. Thus it has a significant industrial impact.

Maintaining the temperature of buffer solutions at a target temperature is made possible by contacting a solution container or a transfer tube through which a buffer solution is carried into the column, with a water bath set to the temperature. In certain environments, it may be preferred to set the temperature of the water bath a few degrees lower than the target temperature when the target temperature is lower than room temperature or a few degrees higher when the target temperature is higher than room temperature. In certain environments, it may be preferred to set the temperature of circulating heat media in a similar manner when controlling the column temperature.

Buffer Solutions

For buffer solutions used above, for example phosphate buffer, Tris buffer, etc. are preferred.

Supports

In the above methods for separating and/or purifying immunoglobulin, it is preferred to use an affinity chromatography column filled with affinity chromatography supports of the present invention prepared by the method described above using "a polypeptide of the present invention, etc." as at least a part of the affinity ligands.

A Gene Encoding "a Polypeptide of the Present Invention, Etc."

A gene encoding "a polypeptide of the present invention, etc." is useful for producing the polypeptide of the present invention ("GG", "nGG containing polypeptides"), a Protein A mutant, specifically in constructing vectors, etc. which can produce these.

In the present invention, a "gene" represents a polynucleotide comprising, as its components, a purine base such as adenine (A) and guanine (G), a pyrimidine base such as thymine (T), uracil (U), and cytosine (C), and a modified base thereof, including a single or a double stranded DNA, a single or a double stranded RNA, a hybrid comprised of a single stranded DNA and a single stranded RNA, and even a chimera in which RNA and DNA are combined together to become a single strand.

In other words, a gene encoding a polypeptide of the present invention may not be necessarily DNA, and may be RNA or a chimera of DNA and RNA, provided that it can directly or indirectly lead to expression of the polypeptide of the present invention (a mutant of the immunoglobulin binding domain and/or a Protein A mutant) by a biotechnological approach. Specifically, the genes may be those shown in the sequence table as a single strand as well as those having a complementary sequence thereof, and they may be used as a double strand together with such a complementary sequence, including a hybrid of DNA and RNA.

A "gene" of the present invention can be easily prepared using a known technique after determining polynucleotide sequences for the polypeptides of the present invention ("GG", "nGG content polypeptides") or Protein A mutants from their amino acid sequences.

Specifically, a "gene" of the present invention can be prepared by the methods such as artificially synthesizing it according to the conventional methods using a DNA synthesizer etc.; introducing a mutation such as deletion, substitution, addition, and insertion, etc. into the nucleotide part on the gene for naturally occurring Protein A or its immunoglobulin binding domain, which corresponds to a mutated site on "a polypeptide of the present invention, etc." using the gene as a template; or permitting reverse transcriptase, DNA polymerase, or RNA polymerase, etc. to synthesize a target sequence using a sequence complementary to the target sequence.

A Method to Produce Protein a Mutants or the Mutants of Immunoglobulin Binding Domain Thereof of the Present Invention for Immunoglobulin Purification A method to produce Protein A mutants or mutants of the immunoglobulin binding domain thereof of the present invention for immunoglobulin purification is characterized in that it includes the steps of (1), (2) below.

(1) A step of selecting a Protein A mutant or a mutant of the immunoglobulin binding domain of Protein A.

(2) A step of selecting those showing a change in immunoglobulin binding properties in response to a temperature change under the conditions of pH 5-9, below 60° C.

The order to perform (1) and (2) does not matter, but in view of efficiency, it is preferred to perform (1) first then followed by (2).

In (1), a mutant can be selected from various kinds of novel mutants or known mutants.

In (2), the methods of selecting those showing a change in immunoglobulin binding properties in response to a temperature change include, for example, a method to determine whether immunoglobulin will be eluted or not by allowing immunoglobulin to bind to a candidate Protein A mutant produced in (1) under the conditions of a certain temperature, and then increasing the temperature up to a temperature lower than 60° C. where the structure of immunoglobulin becomes unstable, and then washing with buffer.

Specifically, it is preferred to select, for example, those having a lower amount of bound immunoglobulin in an elevated temperature range of 30-45° C., preferably 32-38° C., more preferably around 37° C., compared with the amount of bound immunoglobulin in a low temperature range of 0-15° C., preferably 0-8° C., more preferably around 5° C.

An Apparatus for Immunoglobulin Purification of the Present Invention

An apparatus for immunoglobulin purification of the present invention includes following (M) and (N) as constituent requirements.

(M) An affinity chromatography column containing the affinity chromatography material according to the present invention.

(N) A means by which the temperature inside a column can be controlled and/or a means by which the temperature inside the column can be determined.

The means of (N) by which the temperature inside a column can be controlled include temperature control means such as an automatic temperature regulator (thermostat) or other thermoregulators which is built in or connected with the column, as well as a circulation jacket which is arranged so that a temperature regulated circulating solution directly or indirectly contacts with the column.

In addition, other than these, a temperature control means may be those built in or connected with the containers for a sample to be separated/purified, a wash solution, an eluting solution, which are to flow through the column.

The means of (N) by which the temperature inside a column can be measured may represent not only a means to directly measure the temperature inside the column, but also a means to indirectly determine the temperature inside the column by measuring the temperature of a sample to be separated/purified, a wash solution, an eluting solution which are to be applied to the column, and an eluted solution from the column.

The means to directly measure the temperature inside a column include, for example, various kinds of internal thermometers within the column exemplified by micro thermometers such as a temperature sensor, and other temperature measurement means, etc.

The means to indirectly measure the temperature inside a column include in particular various kinds of thermometers exemplified by micro thermometers such as a temperature sensor, and other temperature measurement means, etc. to measure the temperature within the containers for a sample to be separated/purified, a wash solution, an eluting solution, which are to flow through the column, and the temperature within the collection container for an eluted solution from the column, where the temperature measurement means are not necessarily physically connected with the containers.

EXAMPLES

Example 1

A Polypeptide of the Present Invention Based on B Domain

Preparation of DNA for a Polypeptide of the Present Invention

FIG. 1 shows the procedure for constructing a full length double stranded DNA corresponding to an amino acid sequence for a mutant of the immunoglobulin binding B domain of the present invention.

The DNA sequence corresponding to the amino acid sequence of "a polypeptide of the present invention (SEQ ID NO 9)" where Leu at position 19 and position 22 in B domain (SEQ ID NO 1) were each replaced with Gly, and Gly at position 29 in B domain was replaced with Ala, which was optimized for expression in *E. Coli* hosts, was partly synthesized into the separate oligonucleotides of SEQ ID NOs 3 to 8 shown in Table 1 below. Oligonucleotide SEQ ID NOs 3, 5, and 7 encode a sense side of the DNA sequence, and Oligonucleotide SEQ ID NOs 4, 6, and 8 encode an antisense side of the DNA sequence.

TABLE 1

| SEQ ID NO | DNA SEQUENCE |
|---|---|
| SEQ ID NO 3 | GTG CCG CGC CAT ATG GCC GAT AAC AAA TTT AAT AAA GAA CAG C |
| SEQ ID NO 4 | CGC ACC ATG CAA GAT CTC ATA GAA CGC ATT TT G CTG TTC TTT ATT AAA TTT GTT ATC |
| SEQ ID NO 5 | C TAT GAG ATC TTG CAT GGT CCG AAT GGC AAT GAG GAA CAA CGT AAC GCG TTT ATT CAG TCT |
| SEQ ID NO 6 | CAG GTT GGC GCT CTG ACT CGG ATC ATC CTT GAG AGA CTG AAT AAA CGC GTT ACG TTG TTC |
| SEQ ID NO 7 | CCG AGT CAG AGC GCC AAC CTG TTA GCT GAA GCG AAG AAA CTG AAC GAT GCA CAG GCG |
| SEQ ID NO 8 | GTA CAG CCG GGA CTC GAG TTA CGC TTT AGG CGC CTG TGC ATC GTT CAG TTT CTT CGC |

The oligonucleotides having an adjacent SEQ ID NO in the DNA sequence corresponding to the amino acid sequence for the polypeptide of Example 1 have 21 to 27 base pairs being mutually complementary as shown in Table 1 and FIG. 1, and are designed to anneal as shown in the figure under the appropriate temperature conditions.

The full length double stranded DNA comprising the sequence corresponding to the amino acid sequence for the polypeptide of the present invention was completed by performing 15 to 20 temperature cycles of denaturation, annealing, and extension like PCR on a sample solution where DNA polymerase or the like is added to a mixture of the synthetic oligonucleotides, and filling the gaps between the oligonucleotides to complete the double stranded DNA complementary each other. The DNA sequence for the polypeptide was designed such that the N terminus side may serve as a recognition site of NdeI and the C terminus side may serve as a recognition site of XhoI.

After digesting the both ends of the DNA with restriction enzymes (NdeI and XhoI), agarose gel electrophoresis was performed to purify the full length double stranded DNA corresponding to the mutant of the immunoglobulin binding B domain of the present invention using QIAquick Gel Extraction Kit (QIAGEN, Japan).

Preparation of a Vector Expressing a Polypeptide of the Present Invention

FIG. 2 shows the procedure for constructing an expression vector pET-GG containing the full length double stranded DNA corresponding to the amino acid sequence of the immunoglobulin binding domain of the present invention. The cloning site of a plasmid pET15b (Merck, Japan) was cut using restriction enzymes (NdeI and XhoI). After purifying the plasmid using QIAquick DNA cleanup system (QIAGEN, Japan), a ligation reaction where the full length double stranded DNA corresponding to the amino acid sequence of the polypeptide of the present invention is ligated into the cloning site in the plasmid was performed using T4 DNA ligase to obtain a plasmid vector capable of expressing the polypeptide of the present invention (hereafter may be referred to as "GG"), which was designated as "pET-GG." FIG. 3 shows the cloning site of pET-GG.

Transformation and Amplification of a Plasmid

XL1-Blue competent cells (Nippon gene, Japan) were transformed with the plasmid vector obtained above by the heat shock method. The reaction products were allowed to grow for 18 hours on a LB plate containing 50 mg/l of ampicillin (hereafter abbreviated as Amp-LB). Colonies grown on the plate were inoculated into Amp-LB liquid media, and were allowed to grow for 18 hours to select an *E. coli* colony transformed with the plasmid vector of the present invention.

Purification of a Plasmid Vector

An expression vector pET-GG for the polypeptide of the present invention was purified from the *E. coli* strain using QIAprep Spin miniprep kit (QIAGEN, Japan). The expression vector can be used to express the polypeptide of the present invention as described below.

Polypeptide Expression and Tag Removal

A polypeptide of the present invention is produced by, for example, transforming *E. coli* suitable for expression, such as BL21 (DE3) used in Example 2 below, with pET-GG prepared using pET15b plasmid. In this case, it is produced as a fusion polypeptide where a His tag (6×His) and the recognition sequence for a protein restriction enzyme, thrombin, etc. are fused at the N terminus side.

Note that the His tag can be removed from the polypeptide using thrombin if necessary. In that case, Gly and Ser will be left to the N terminus side of the polypeptide.

Example 2

"2GG Containing Polypeptide"

Production of a fusion polypeptide in which two polypeptides are connected can be performed in the following manner.

A Plasmid which Produces a Fusion Polypeptide in which Two Polypeptides are Connected In order to produce a "2GG containing polypeptide" of the present invention, an additional gene for a polypeptide of the present invention is introduced into the plasmid of Example 1 capable to produce "GG."

The DNA sequence of the polypeptide prepared in Example 1 was designed so that the N terminus side may serve as a recognition site of NdeI and the C-terminus side may serve as a recognition site of XhoI, while the recognition site of BamHI is located downstream of the recognition site of XhoI in pET-GG. Therefore, pET-GG is digested with XhoI and BamHI, while the additional DNA sequence of the polypeptide to be introduced is re-designed so that the N-terminus side may serve as a recognition site of XhoI and the C-terminus side may serve as a recognition site of BamHI. Then the DNA of the polypeptide is inserted at the C-terminus side of DNA of the existing polypeptide to create pET-2GG. T4 DNA ligase can be used ligate a digested plasmid with DNA of the polypeptide of the present invention.

A fusion polypeptide produced by pET-2GG will be in the form of His tag (6×His)-thrombin recognition site-polypeptide-polypeptide.

Example 3

"3GG Containing Polypeptide"

Preparation of a fusion polypeptide containing 3 polypeptides can be easily performed as described below.

The recognition site of XhoI between the two polypeptide genes in pET-2GG is treated by modifying the site using site directed mutagenesis so that the site may not be cut there. The "2GG containing polypeptide" gene is amplified by the standard PCR method using primers which are designed so that the N terminus side may serve as a recognition site of XhoI and the C-terminus side may serve as a recognition site of BamHI. It is inserted into pET-GG digested with XhoI and BamHI. The resulting plasmid is pET-3GG, and a fusion polypeptide to be expressed will be in the form of His tag-thrombin recognition site-polypeptide-polypeptide-polypeptide.

Example 4

"4GG Containing Polypeptide"

Preparation of a fusion polypeptide containing 4 polypeptides can be performed in a similar way as in Example 3, for example, by preparing a "3GG containing polypeptide" gene using pET-3GG.

Example 5

Expression and Purification of a Protein of Interest

With the constructed plasmid pET-GG, BL21 (DE3) competent cells (Nippon gene, Japan) were transformed by the heat shock method, and the resulting reaction products were allowed to grow on an Amp-LB media plate for 18 hours. Colonies grown on the plate were inoculated into Amp-LB liquid media, and allowed to grow for 18 hours to obtain an *E. coli* strain expressing a polypeptide of the present invention. The *E. coli* strain was inoculated into 2×TY liquid media containing 50 mg/l of ampicillin, and cultured with shaking at 37° C. until absorbance at 600 nm reaches around 0.7 to 0.8. Then, IPTG was added to a final concentration of 1 mM, shaking culture was further continued at 30° C. for 18 hours to express a fusion polypeptide containing the polypeptide of the invention (hereafter designated as "BGG").

Example 6

Purification of a Polypeptide of the Present Invention

*E. coli* cells in which a polypeptide of the present invention was expressed were collected by centrifugation, and suspended in 20 mM phosphate buffer (pH 7.4) containing 20 mM imidazole and 0.5M NaCl. The suspended *E. coli* cells in the suspension were lysed by the freeze-thawing method, and a fusion polypeptide of interest was collected in the supernatant by centrifugation. The supernatant was loaded into a Ni-NTA (QIAGEN, Japan), and the Ni-NTA was washed well with 20 mM phosphate buffer contains 40 mM imidazole and 500 mM NaCl (pH 7.4), and then the polypeptide of the present invention was collected by elution with 20 mM phosphate buffer containing 250 mM imidazole and 500 mM NaCl (pH 7.4). The purity of the polypeptide of the present invention was checked by sodium dodecyl sulfate-polyacrylamide gel electrophoresis (hereafter abbreviated as SDS-PAGE). The concentration of the polypeptide was determined by absorbance of Tyr at 276 nm.

Example 7

Affinity Chromatography Supports of the Present Invention

Immobilization of the ligands comprising a polypeptide of the present invention to affinity chromatography supports was performed using HiTrap NHS-activated HP (GE health care biosciences, Japan). The column was filled with agarose as solid supports to which activated N-hydroxysuccinimide is coupled via a spacer of six atoms. $NHCO_3$ buffer containing 200 mM NaCl (pH 8.3) was used as a coupling agent to immobilize the polypeptide of the present invention to the column.

Example 8

Purification of IgG by Using a Column where the Polypeptides of the Present Invention are Immobilized The temperature inside the column was adjusted to 5° C. by leaving it immersed in a water bath adjusted to 5° C. for sufficient time. 5.0 mg of human IgG (determined by absorbance at 280 nm) was dissolved in 20 mM phosphate buffer containing 100 mM NaCl (pH 7.4) which was similarly adjusted to 5° C. by being immersed in a water bath, and a sample solution thereof was loaded into the column. The column was washed well with 20 mM phosphate buffer containing 100 mM NaCl (pH 7.4) at 5° C., and then transferred into a 37° C. water bath, and human IgG was eluted with 20 mM phosphate buffer containing 100 mM NaCl (pH 7.4) at 37° C. By measuring absorbance at 280 nm of the eluted sample solution, it was found that 4.8 mg of humans IgG was collected.

Note that association/aggregation of IgG was not observed in the eluted sample solution. That is, a yield of 96% was achieved by the separation and/or purification method of the present invention, while IgG was still in the state of being active.

It is a remarkable value considering a recovery ratio of active IgG when conventional Protein A or B domain, etc. is used.

The chromatograph thereof is shown in FIG. 4. In addition, it was found that the separation and/or purification method has an elution speed comparable to the conventional method using a pH change, and can be adequately used for industrial applications.

Examples 9-20

Various Polypeptides of the Present Invention

Various polypeptides of the present invention shown in Table 3 were produced using the template plasmids and primers shown in Table 2 below. Note that an indicated mutated site shows a site different from the polypeptide of SEQ ID NO 2.

Specifically, it was carried out as follows.

Preparation of a Vector Expressing the Polypeptide of SEQ ID NO 2 (PWT)

Using pET-GG prepared in Example 1, a vector (pET-PWT) expressing the polypeptide of SEQ ID NO 2 (PWT) was prepared by using site directed mutagenesis.

This vector is a vector encoding the polypeptide of SEQ ID NO 2, which is a base for a polypeptide of the present invention, and based on it, various other polypeptides of the present invention can be prepared by replicating using primers with a desired mutation introduced. Note that pET-GG prepared in Example 1 was used as a base only for convenience when preparing the vector, and thus it is of course possible to prepare it in other ways.

15 to 20 temperature cycles of denaturation, annealing, and extension as used in PCR were performed with a pair of primers shown in Table 2 using pET-GG as a template. The solution used for the reaction includes substances required for DNA amplification such as pfu turbo DNA polymerase (QIAGEN, Japan) in addition to a template and primers.

As a result of the reaction, obtained was an expression vector for the polypeptide of SEQ ID NO 2 where Gly at position 19 and position 22 in pET-GG were both replaced with Leu. Hereafter, this vector may be referred to as pET-PWT.

Then, XL1-Blue competent cells (Nippon gene, Japan) were transformed with pET-PWT by the heat shock method. The reaction products were cultured on an Amp-LB media plate at 37° C. for about 18 hours.

Colonies grown on the plate were inoculated into Amp-LB liquid media, and cultured with shaking at 37° C. for about 18 hours, and then the transformed cells with pET-PWT were selected and allowed for proliferation.

Purification of pET-PWT, Expression of PWT, and Purification of PWT

Purification of pET-PWT was performed in a similar way as purification of pET-GG. Expression and purification, etc. of the polypeptide encoded in pET-PWT were performed in a similar way as pET-GG described in Example 5 and Example 6. The expressed polypeptide is a fusion peptide which is similar to the polypeptide (BGG) expressed using pET-GG.

Preparation of Plasmid Vectors for the Polypeptides of Examples 9-20, and Expression and Purification of the Polypeptides Plasmids expressing the polypeptides of Examples 9-20 were prepared in a similar way as pET-PWT using a combination of each template plasmid and primers having a desired mutation as shown in Table 2. Amplification and purification of these were performed in a similar way as pET-GG. Expression and purification of the polypeptides using those plasmid vectors were performed in a similar way as pET-GG. These expressed polypeptides of Examples 9-20 are fused peptides which are similar to the polypeptide (BGG) expressed using pET-GG.

Affinity Chromatography Supports of PWT and the Polypeptides of Examples 9-20

Immobilization of PWT and the above mutants to affinity chromatography supports was performed in a similar way as in Example 7.

Purification of IgG Using the Columns in which the Polypeptides of PWT and Examples 9-20 are Immobilized The temperature inside the column was adjusted to 1-5° C. by leaving it immersed in a water bath adjusted to 2-5° C. for sufficient time. 1.6 mg of human IgG (Fluka) was dissolved in 20 mM phosphate buffer containing 100 mM NaCl (pH 7.4) which was similarly adjusted to 1-5° C. in a water bath, and a sample solution thereof was loaded into the column. The column was washed well with 20 mM phosphate buffer containing 100 mM NaCl (pH 7.4) at 1-5° C., and then transferred into a 37° C. water bath, and then human IgG was eluted with 20 mM phosphate buffer containing 100 mM NaCl (pH 7.4) at 37° C. The recovery ratio of human IgG (a purification yield) was determined by measuring the volume of the eluted sample solution and absorbance at 280 nm.

The IgG recovery ratios for the polypeptide of each of Examples 9-20 are shown in Table 4. In addition, the IgG recovery ratio for the polypeptide of Example 5 is also shown in Table 4 for comparison. Furthermore, the correlation between the difference in the Gibbs free energy for denaturation and the recovery ratios of IgG was shown in FIGS. 5 and 6.

On the Recovery Ratio of BGG (L19G+L22G)

Note that in Example 8 (purification of IgG), when human IgG was purified using BGG of Example 5, BGG showed an IgG recovery ratio of 96%. When IgG recovery experiments were again carried out using BGG of Example 5 under the same conditions as the polypeptides of Examples 9-20 this time, the recovery ratio was found to be repeatedly about 75% as shown in Table 4 even if it was checked for many times.

As a result of analyzing human IgG previously used in Example 8 with a gel filtration column in order to investigate this reason, it became clear that Example 8 contained impurities which were not seen in human IgG used in this Example (a product from a different package).

Therefore, it appears that the different recovery ratios when BGG was used was caused merely due to the presence or absence of impurities in immunoglobulin to be purified.

The Values of $\Delta\Delta G_{PWT}$ for Each Mutant of Protein, and the IgG Recovery Ratios $\Delta\Delta G_{X\text{-}PWT}$ (a value where $\Delta G_{PWT}$ for PWT is subtracted from $\Delta G_X$ for a target mutant X) for each of the polypeptides of Example 5 and Examples 9-20 are shown in Table 4 together with the IgG recovery ratios, etc. Note that these values were computed using ΔGs for known mutants of B domain of Protein A, etc. (nonpatent literatures 3 and 4) as described above.

As clear from this Table 4, we have found that a $\Delta\Delta G_{X\text{-}PWT}$ ranging from about −12.6 kcal/mol (BGA21) to about −7.8 kcal/mol (BGG17) is required in order to obtain an IgG recovery ratio of 55% or more under these conditions. Further, we found that a recovery ratio of 91% was achieved when $\Delta\Delta G_{X\text{-}PWT}$ was about −9.2 kcal/mol (BGG13).

Note that a recovery ratio is predicted from FIG. 5 to become maximum probably when $\Delta\Delta G_{X\text{-}PWT}$ is about −11 to −10 kcal/mol, in particular around −10.2 kcal/mol.

The Values of $\Delta\Delta G_{X\text{-}BGG}$ for the Polypeptides of the Present Invention, and the Recovery Ratios of IgG BGG (Example 5), BGG11 (Example 9), BLG18 (Example 14), BLG19 (Example 15), BLG21 (Example 16), BLG28 (Example 17), and BLG32 (Example 18) have a recovery ratio of 72 to 78%. All of these polypeptides contain a mutation in which Leu at position 22 is replaced by Gly.

Because ΔGs for such polypeptides of the present invention in which Leu at position 22 were substituted to Gly were difficult to be determined by the level of the current standard technologies since they are significantly unstable as compared with PWT. Therefore, it is difficult to determine $\Delta\Delta G_{X\text{-}PWT}$ for the polypeptides of the present invention containing this mutation. However, it is possible to compute the relative difference in ΔG based on one of the polypeptides of those.

For example, the relative difference in ΔG based on BGG of Example 5, i.e., $\Delta\Delta G_{X\text{-}BGG}$ can be computed from the values in nonpatent literatures 3 and 4. As a result of the calculation, we have found that the above mutants (BGG11

(Example 9) and BLG18 (Example 14), BLG19 (Example 15), BLG21 (Example 16), BLG28 (Example 17), and BLG32 (Example 18)) show $\Delta\Delta G_{X-BGG}$ within the range from −0.5 to +1.5 kcal/mol (refer to Table 4). Therefore, even though it is difficult to determine $\Delta\Delta G_{X-PWT}$, we have found that a similar recovery ratio can be obtained if the stability compared with that of BGG lies within the range from −0.5 to +1.5 kcal/mol.

From FIG. 6 illustrating the results from Table 4, we have found that a similar recovery ratio can also be expected if −1 kcal/mol$\leqq\Delta\Delta G_{X-BGG}\leqq$1.5 kcal/mol.

The Range of $\Delta\Delta G_{X-PWT}$ where a High Recovery Ratio can be Obtained In addition, since BGG13 whose $\Delta\Delta G_{X-PWT}$ is −9.2 kcal/mol has a recovery ratio of 91%, mutants other than BGG13 can be expected to have a similar high recovery ratio if their values of $\Delta\Delta G_{X-PWT}$ are in that range.

Table 4 shows the Gibbs free energy for denaturation of each of the polypeptides, and the results of purification of IgG using the polypeptides.

Tests for Association/Aggregation of the Eluted Antibody

Note that as a result of analyzing the eluted sample solutions using a gel filtration column (Superdex 200 10/300GL, GE health care biosciences, Japan), no development of association/aggregation of IgG was observed in the eluted sample solutions.

Based on the above results, FIGS. 5 and 6 show the correlation between the Gibbs free energy for denaturation and the immunoglobulin purification yield.

Note that the polypeptide of SEQ ID NO 1 differs from the polypeptide of SEQ ID NO 2 only in that Gly at position 29 in SEQ ID NO 1 is changed to Ala in SEQ ID NO 2 as described above. In addition, the Gibbs free energy for denaturation of SEQ ID NO 1 is lower than SEQ ID NO 2 only by 0.9 kcal/mol. Therefore, considering that the above mutants based on SEQ ID NO 2 showed a high immunoglobulin recovery ratio by a temperature change in the example descried below, a mutant based on SEQ ID NO 1 where position 29 in the mutants of the examples is changed to Gly will also have a preferred Gibbs free energy for denaturation as descried above, and is thought to have a similar capability.

Example 21

Other Polypeptides of the Present Invention

A polypeptide was prepared where Asn at position 23 in BGG13 of Example 11 was replaced with Thr using site directed mutagenesis as descried above. Specifically, as shown in Table 2, it was prepared in a similar way as the polypeptides of Examples 9-21 using pET-GG13 as a template plasmid, and SEQ ID NO 44 and SEQ ID NO 45 as primers for the polypeptide. The resulting polypeptide is designated as NT23BGG13 (SEQ ID NO 46) (see Table 3).

Test Example 1

Alkaline Resistance Tests of a Polypeptide of the Present Invention

The changes in purification efficiency caused by alkaline wash (an alkaline resistance of a polypeptide) were compared by performing multiple cycles of immunoglobulin purification and washing the column by alkaline between the cycles using each of BGG13 from Example 11 and NT23BGG13 from Example 21.

The same amount of IgG (1.0 mg) (Fluka) was loaded each time into a column (a volume of 1 ml) to which BGG13 or NT23BGG13 was coupled, and binding and washing were carried out at 4° C., and then the amount of eluted IgG at 37° C. was determined. A method of determination will be explained below. For a buffer solution, a buffer solution of 20 mM Phosphate, 150 mM NaCl, pH 7.0 was used. The flow rate was 1.0 ml/min. First, the amount of eluted IgG before NaOH treatment was determined. 0.1M NaOH was contacted with the column only for a predetermined period of time. Next, the same amount of IgG as the previous time was loaded into the column, followed by determining the amount of eluted IgG at 37° C. in a similar manner, and then 0.1 M NaCl was allowed to make contact with the column for a certain time. NaOH treatment was conducted at room temperature.

The amount of eluted IgG was determined by computing the peak area of eluted IgG on a chromatograph using a function of the chromatographic analysis software Primeview Evaluation (GE health care biosciences, Japan). This eluted amount was defined as the purification capacity of the column under the corresponding conditions.

Then, for each of BGG13 and NT23BGG13, "the contact time passed until the purification capacity after NaOH treatment becomes half of the capacity before the treatment" (a half-life of purification capacity) was compared, and we found that the half-life for NT23BGG13 was improved by 1.4 times than that for BGG13. Note that the immunoglobulin recovery ratio for NT23BGG13 before NaOH treatment was 90%, which was comparable to BGG13.

Thus, from the above results, it could be confirmed that a substitution of Asn to Thr in the polypeptide can provide "the ability to change immunoglobulin binding properties by changing temperature" as described above, as well as the improvement in the alkaline resistance of the polypeptide.

TABLE 2

| Example | Polypeptide Name to be Expressed (SEQ ID NO) | Amino Acid mutation (Based on PWT) | Plasmid Name | Template Plasmid | Primers |
|---|---|---|---|---|---|
| | PWT (SEQ ID NO 2) | — | pET-PWT | pET-GG | SEQ ID NO 22: TAT GAG ATC TTG CAT CTT CCG AAT CTG AAT GAG GAA CAA CGT SEQ ID NO 23: ACG TTG TTC CTC ATT CAG ATT CGG AAG ATG CAA GAT CTC ATA |
| 9 | BGG11 (SEQ ID NO 10) | L19A + L22G | pET-GG11 | pET-GG | SEQ ID NO 24: TAT GAG ATC TTG CAT GCT CCG AAT GGC AAT GAG SEQ ID NO 25: CTC ATT GCC ATT CGG AGC ATG CAA GAT CTC ATA |

TABLE 2-continued

| Example | Polypeptide Name to be Expressed (SEQ ID NO) | Amino Acid mutation (Based on PWT) | Plasmid Name | Template Plasmid | Primers |
|---|---|---|---|---|---|
| 10 | B G G 1 2 (SEQ ID NO 11) | L22G | pET-GG12 | pET-GG | SEQ ID NO 26: TAT GAG ATC TTG CAT **CTT** CCG AAT GGC AAT GAG SEQ ID NO 27: CTC ATT GCC ATT CGG AAG ATG CAA GAT CTC ATA |
| 11 | B G G 1 3 (SEQ ID NO 12) | L19G + L22A | pET-GG13 | pET-GG | SEQ ID NO 28: TTG CAT **GGT** CCG AAT GCC AAT GAG GAA CAA CGT SEQ ID NO 29: ACG TTG TTC CTC ATT GGC ATT CGG ACC ATG CAA |
| 12 | B G G 1 4 (SEQ ID NO 13) | L19G | pET-GG14 | pET-GG | SEQ ID NO 30: TTG CAT **GGT** CCG AAT CTC AAT GAG GAA CAA CGT SEQ ID NO 31: ACG TTG TTC CTC ATT GAG ATT CGG ACC ATG CAA |
| 13 | B G G 1 7 (SEQ ID NO14) | L19A + L22A | pET-GG17 | pET-GG | SEQ ID NO 32: TAT GAG ATC TTG CAT **GCT** CCG AAT GCG AAT GAG GAA CAA CGT SEQ ID NO 33: ACG TTG TTC CTC ATT CGC ATT CGG AGC ATG CAA GAT CTC ATA |
| 14 | B L G 1 8 (SEQ ID NO 15) | L22G + F30A | pET-LG18 | pET-GG12 | SEQ ID NO 34: GAA CAA CGT AAC GCG *GCT* ATT CAG TCT CTC AAG SEQ ID NO 35: CTT GAG AGA CTG AAT AGC CGC GTT ACG TTG TTC |
| 15 | B L G 1 9 (SEQ ID NO 16) | L22G + F30G | pET-LG19 | pET-GG12 | SEQ ID NO 36: GAA CAA CGT AAC GCG *GGT* ATT CAG TCT CTC AAG SEQ ID NO 37: CTT GAG AGA CTG AAT ACC CGC GTT ACG TTG TTC |
| 16 | B L G 2 1 (SEQ ID NO 17) | L22G + L51G | pET-LG21 | pET-GG12 | SEQ ID NO 38: GCT GAA GCG AAG AAA ***GGT*** AAC GAT GCA CAG GCG SEQ ID NO 39: CGC CTG TGC ATC GTT ACC TTT CTT CGC TTC AGC |
| 17 | B L G 2 8 (SEQ ID NO 18) | L22G + Q26G | pET-LG28 | pET-GG12 | SEQ ID NO 40: AAT GGC AAT GAG GAA GGC CGT AAC GCG *TTT* ATT SEQ ID NO 41: AAT AAA CGC GTT ACG GCC TTC CTC ATT GCC ATT |
| 18 | B L G 3 2 (SEQ ID NO 19) | L22G + R27G | pET-LG32 | pET-GG12 | SEQ ID NO 42: GGC AAT GAG GAA CAA GGC AAC GCG *TTT* ATT CAG SEQ ID NO 43: CTG AAT AAA CGC GTT GCC TTG TTC CTC ATT GCC |
| 19 | B G A 1 9 (SEQ ID NO 20) | L19G + L22A + F30G | pET-GA19 | pET-GG13 | SEQ ID NO 36: GAA CAA CGT AAC GCG GGT ATT CAG TCT CTC AAG SEQ ID NO 37: CTT GAG AGA CTG AAT ACC CGC GTT ACG TTG TTC |
| 20 | B G A 2 1 (SEQ ID NO 21) | L19G + L22A + L51G | pET-GA21 | pET-GG13 | SEQ ID NO 38: GCT GAA GCG AAG AAA ***GGT*** AAC GAT GCA CAG GCG SEQ ID NO 39: CGC CTG TGC ATC GTT ACC TTT CTT CGC TTC AGC |
| 21 | N T 2 3 B G G 1 3 (SEQ ID NO 46) | L19G + L22A + N23T | pET-NT23 | pET-GG13 | SEQ ID NO 44: CAT GGT CCG AAT GCC ACT GAG GAA CAA CGT AAC SEQ ID NO 45: GTT ACG TTG TTC CTC AGT GGC ATT CGG ACC ATG |

Double underline: indicates the position into which an amino acid mutation is introduced using the primers.
Single underline: corresponds to the position where an mutation is already introduced by the template plasmid.
Bold: corresponds to position 19 in the polypeptide.
Italic: corresponds to position 30 in the polypeptide.
Bold & Italic: corresponds to position 51 in the polypeptide.

TABLE 3

| SEQ ID NO | |
|---|---|
| 110 | ADNKFNKEQQNAFYEILH**A**PNGNEEQRNAFIQSLKDDPSQSANLLAEAKKLNDAQAPKA |
| 11 | ADNKFNKEQQNAFYEILHLPN**G**NEEQRNAFIQSLKDDPSQSANLLAEAKKLNDAQAPKA |
| 12 | ADNKFNKEQQNAFYEILH**G**PN**A**NEEQRNAFIQSLKDDPSQSANLLAEAKKLNDAQAPKA |
| 13 | ADNKFNKEQQNAFYEILH**G**PNLNEEQRNAFIQSLKDDPSQSANLLAEAKKLNDAQAPKA |
| 14 | ADNKFNKEQQNAFYEILH**A**PN**A**NEEQRNAFIQSLKDDPSQSANLLAEAKKLNDAQAPKA |
| 15 | ADNKFNKEQQNAFYEILHLPN**G**NEEQRNA**A**IQSLKDDPSQSANLLAEAKKLNDAQAPKA |
| 16 | ADNKFNKEQQNAFYEILHLPN**G**NEEQRNA**G**IQSLKDDPSQSANLLAEAKKLNDAQAPKA |
| 17 | ADNKFNKEQQNAFYEILHLPN**G**NEEQRNAFIQSLKDDPSQSANLLAEAKKGNDAQAPKA |
| 18 | ADNKENKEQQNAFYEILHLPN**G**NEE**G**RNAFIQSLKDDPSQSANLLAEAKKLNDAQAPKA |
| 19 | ADNKFNKEQQNAFYETLHLPN**G**NEEQ**G**NAFIQSLKDDPSQSANLLAEAKKLNDAQAPKA |
| 20 | ADNKFNXEQQNAFYEILH**G**PN**A**NEEQRNA**G**IQSLKDDPSQSANLLAEAKKLNDAQAPKA |
| 21 | ADNKENKEQQNAFYEILH**G**PN**A**NEEQRNAFIQSLKDDPSQSANLLAEAKKGNDAQAPKA |
| 46 | ADNKFNKEQQNAFYEILH**G**PN**A**TEEQRNAFIQSLKDDPSQSANLLAEAKKLNDAQAPKA |

Bold: An amino acid which differs from that in the corresponding position in SEQ ID NO 2

TABLE 4

| Example | Polypeptide Name to be Expressed | SEQ ID NO | IgG Recovery Ratio (%) | $\Delta\Delta G_{X\text{-}PYT}$ (kcal/mol) | $\Delta\Delta G_{X\text{-}BGG}$ (kcal/mol) |
|---|---|---|---|---|---|
| 5 | BGG | 9 | 75 | N/D | N/D |
| 9 | BGG11 | 10 | 72 | N/D | 1.5 |
| 10 | BGG12 | 11 | 38 | N/D | 4.2 |
| 11 | BGG13 | 12 | 91 | −9.2 | N/D |
| 12 | BGG14 | 13 | 11 | −4.2 | N/D |
| 13 | BGG17 | 14 | 55 | −7.8 | N/D |
| 14 | BLG18 | 15 | 73 | N/D | 1.5 |
| 15 | BLG19 | 16 | 75 | N/D | −0.5 |
| 16 | BLG21 | 17 | 78 | N/D | 0.8 |
| 17 | BLG28 | 18 | 78 | N/D | 0.6 |
| 18 | BLG32 | 19 | 78 | N/D | 1.3 |
| 19 | BGA19 | 20 | 30 | −13.9 | N/D |
| 20 | BGA21 | 21 | 55 | −12.6 | N/D |

Note that since the IgG recovery ratios for each of the polypeptides in Examples above are 30% or more, binding ratios with immunoglobulin before elution are at least 30% or more. In other words, it was confirmed that the ratios are at least 30% or more of "the binding ratio with immunoglobulin for the polypeptide of SEQ ID NO 1 or SEQ ID NO 2." It is because they correspond to 30% or more of it even if a binding ratio with immunoglobulin for SEQ ID NO 1 or SEQ ID NO 2 is 100%.

INDUSTRIAL APPLICABILITY

"The polypeptide of the present invention, etc." which can efficiently purify highly pure immunoglobulin is very useful in the fields of life science research, pharmaceuticals, and laboratory tests, etc.

BRIEF DESCRIPTION OF THE DRAWINGS

FIG. 1 shows the procedure for constructing a double stranded DNA corresponding to a full length polypeptide of the present invention.

FIG. 2 shows the procedure for constructing an expression plasmid containing a double stranded DNA corresponding to a full length polypeptide of the present invention.

FIG. 3 shows the cloning site of pET-GG.

FIG. 4 shows experimental data for actual immunoglobulin purification using a polypeptide of the present invention. All the buffers used were neutral, and a neutral buffer at 5° C. was used in loading and washing, and at 37° C. in elution.

FIG. 5 shows the correlation between the difference in the Gibbs free energy for denaturation ($\Delta\Delta G_{X\text{-}PWT}$) and the IgG recovery ratio (the immunoglobulin purification yield).

FIG. 6 shows the correlation between the difference in the Gibbs free energy for denaturation ($\Delta\Delta G_{X\text{-}BGG}$) and the IgG recovery ratio (the immunoglobulin purification yield).

FIG. 7 shows the sequences of SEQ ID NO 1 (B domain), SEQ ID NO 2 (PWT), and SEQ ID NO 9 (BGG).

What is claimed is:

1. A method for separating and/or purifying immunoglobulin using affinity chromatography, comprising:

eluting the immunoglobulin by changing temperature using affinity chromatography material comprising polypeptide, which is a mutant of the polypeptide of SEQ ID NO 1 or SEQ ID NO 2 wherein its immunoglobulin binding properties can be altered by changing temperature under the conditions of pH 5-9, below 60° C.

2. The method for separating and/or purifying immunoglobulin according to claim 1, wherein the affinity chromatography material is used under the conditions of pH 5-9, below 60° C.

* * * * *